(12) United States Patent
Feinstein et al.

(10) Patent No.: US 8,278,287 B2
(45) Date of Patent: Oct. 2, 2012

(54) SIRNA COMPOUNDS FOR INHIBITING NRF2

(75) Inventors: Elena Feinstein, Rehovot (IL); Igor Mett, Rehovot (IL); Hagar Kalinski, Rishon-le-Zion (IL)

(73) Assignee: Quark Pharmaceuticals Inc., Fremont, CA (US)

( * ) Notice: Subject to any disclaimer, the term of this patent is extended or adjusted under 35 U.S.C. 154(b) by 18 days.

(21) Appl. No.: 12/988,307

(22) PCT Filed: Apr. 6, 2009

(86) PCT No.: PCT/IL2009/000387
§ 371 (c)(1),
(2), (4) Date: Jan. 5, 2011

(87) PCT Pub. No.: WO2009/144704
PCT Pub. Date: Dec. 3, 2009

(65) Prior Publication Data
US 2011/0105591 A1    May 5, 2011

Related U.S. Application Data

(60) Provisional application No. 61/124,196, filed on Apr. 15, 2008, provisional application No. 61/194,495, filed on Sep. 25, 2008.

(51) Int. Cl.
A61K 31/70 (2006.01)
C07H 21/02 (2006.01)
C07H 21/04 (2006.01)
(52) U.S. Cl. ............ 514/44 A; 536/24.1; 536/24.5
(58) Field of Classification Search ............ 514/44; 536/24.1, 24.5
See application file for complete search history.

(56) References Cited

U.S. PATENT DOCUMENTS

| | | |
|---|---|---|
| 5,753,789 A | 5/1998 | Chu et al. |
| 5,874,277 A | 2/1999 | Shintani et al. |
| 5,891,683 A | 4/1999 | Usman et al. |
| 5,898,031 A | 4/1999 | Crooke |
| 5,998,203 A | 12/1999 | Matulic-Adamic et al. |
| 6,068,990 A | 5/2000 | Shintani et al. |
| 6,107,094 A | 8/2000 | Crooke |
| 6,117,657 A | 9/2000 | Usman et al. |
| 6,235,886 B1 | 5/2001 | Manoharan et al. |
| 6,251,666 B1 | 6/2001 | Beigelman |
| 6,268,490 B1 | 7/2001 | Imanishi et al. |
| 6,506,559 B1 | 1/2003 | Fire |
| 6,586,238 B1 | 7/2003 | Matulic-Adamic et al. |
| 6,602,858 B2 | 8/2003 | Beigelman |
| 7,056,704 B2 | 6/2006 | Tuschl et al. |
| 7,078,196 B2 | 7/2006 | Tuschl et al. |
| 7,335,765 B2 | 2/2008 | Kaneko et al. |
| 7,452,987 B2 | 11/2008 | Giese et al. |
| 7,749,977 B2 | 7/2010 | Yehiely et al. |
| 7,812,002 B2 | 10/2010 | Feinstein |
| 7,893,245 B2 | 2/2011 | Giese et al. |
| 8,090,542 B2 | 1/2012 | Khvorova et al. |
| 8,097,710 B2 | 1/2012 | Baulcombe et al. |
| 2002/0164576 A1 | 11/2002 | Pederson et al. |
| 2003/0027783 A1 | 2/2003 | Zernicka-Goetz et al. |
| 2003/0108923 A1 | 6/2003 | Tuschl et al. |
| 2004/0005579 A1 | 1/2004 | Birse et al. |
| 2004/0219569 A1 | 11/2004 | Yehiely et al. |
| 2004/0229266 A1 | 11/2004 | Tuschl et al. |
| 2004/0265839 A1 | 12/2004 | Mello et al. |
| 2005/0004064 A1 | 1/2005 | Tei et al. |
| 2005/0020525 A1 | 1/2005 | McSwiggen et al. |
| 2005/0037988 A1 | 2/2005 | Zamore et al. |
| 2005/0080246 A1 | 4/2005 | Allerson et al. |
| 2005/0181382 A1 | 8/2005 | Zamore et al. |
| 2005/0223427 A1 | 10/2005 | Leake et al. |
| 2006/0058266 A1 | 3/2006 | Manoharan et al. |
| 2006/0217331 A1 | 9/2006 | Vargeese et al. |
| 2006/0292586 A1 | 12/2006 | Schroth et al. |
| 2006/0293511 A1 | 12/2006 | Dellinger |
| 2007/0031844 A1 | 2/2007 | Khvorova et al. |
| 2007/0042418 A1 | 2/2007 | Yehiely et al. |
| 2007/0098728 A1 | 5/2007 | Pedersen et al. |
| 2007/0185047 A1 | 8/2007 | Bhat et al. |
| 2009/0215864 A1 | 8/2009 | Feinstein |
| 2010/0047368 A1 | 2/2010 | Biswal et al. |
| 2010/0215588 A1 | 8/2010 | Skaliter |
| 2010/0292301 A1 | 11/2010 | Feinstein et al. |
| 2011/0105591 A1 | 5/2011 | Feinstein et al. |
| 2011/0112168 A1 | 5/2011 | Feinstein et al. |
| 2011/0230543 A1 | 9/2011 | Feinstein |

FOREIGN PATENT DOCUMENTS

| | | |
|---|---|---|
| EP | 0540742 A1 | 5/1993 |
| WO | WO 99/14226 | 3/1999 |
| WO | WO 00/44895 | 8/2000 |
| WO | WO 00/44914 | 8/2000 |
| WO | WO 01/68836 | 9/2001 |
| WO | WO 03/064621 | 8/2003 |
| WO | WO 03/070918 | 8/2003 |
| WO | WO 03/074654 | 9/2003 |

(Continued)

OTHER PUBLICATIONS

International Search Report issued by the International Searching Authority (ISA/US) on Apr. 2, 2010 in connection with PCT International Application No. PCT/IL2009/000387.
Written Opinion of the International Searching Authority issued on Apr. 2, 2010 in connection with PCT International Application No. PCT/IL2009/000387, filed Apr. 6, 2009.
International Preliminary Report on Patentability, including an International Preliminary Report on Patentability and Written Opinion of the International Searching Authority date of mailing Oct. 28, 2010.
AB162435, Bos Taurus nrf2 mRNA for NF-E2-related factor-2, complete cds. Dec. 21, 2004. <http://www.ncbi.nlm.nih.gov/nuccore/56744173>.

(Continued)

Primary Examiner — Terra Cotta Gibbs
(74) Attorney, Agent, or Firm — John P. White; Cooper & Dunham LLP

(57) ABSTRACT

The present invention provides chemically modified siRNA compounds that target the Nrf2 gene and pharmaceutical compositions comprising same useful for treating or preventing the incidence or severity of a cancerous disease, particularly various lung cancers.

21 Claims, No Drawings

FOREIGN PATENT DOCUMENTS

| | | |
|---|---|---|
| WO | WO 2006/128041 | 11/2006 |
| WO | WO 2006/129881 A1 | 12/2006 |
| WO | WO 2007/087451 | 8/2007 |
| WO | WO 2008/114262 | 9/2008 |
| WO | WO 2008/124660 | 10/2008 |

OTHER PUBLICATIONS

Gong, P & Cederbaum, A (2006). Nrf2 is Increased by CYP2E1 in Rodent Liver and HepG2 Cells and Protects Against Oxidative Stress Caused by CYP2E1 Hepatology, 43, 144-153.

Amarzguioui et al., (2003) "Tolerance for Mutations and Chemical Modifications in a siRNA". Nucleic Acids Research, 31(2):589-95.

Barik, (2005) "Silence of the Transcripts; RNA Interference in Medicine". Mol. Med 2005, 83:764-773.

Braasch et al., (2003) "RNA Interference in Mammalian Cells by Chemically-Modified RNA". Biochemistry, 42:7967-7975.

Caplen et al., (2001) "Specific Inhibition of Gene Expression by Small Double-Stranded RNAs in Invertebrate Vertebrate Systems". Proc. Natl. Acad. Sci., 98(17):9742-9747.

Chakraborty (2007) "Potentiality of Small Interfering RNAs-(siRNA)as Recent Therapeutic Targets for Gene-Silencing". Current Drug Targets, vol. 8(3):469-82.

Chiu et al., (2003) "siRNA Function in RNAi: a Chemical Modification Analysis". RNA, 9(9):1034-48.

Czauderna et al., (2003) "Structural Variations and Stabilising Modifications of Synthetic siRNAs in Mammalian Cells". Nucleic Acids Research, 31(11):2705-16.

Damha et al., (1991) "Oligonucleotides containing unnatural L-2'—deoxyribose". Tetrahedron Letters, 32(23):2573-76.

Elbashir et al., (2001) "RNA Interference is Mediated by 21-and 22-nucleotide RNAs". Genes & Development, 15:188-200.

Elbashir et al., (2001) "Functional Anatomy of siRNAs for Mediating Efficient RNAi in *Drosophila melanogaster* Embryo Lysate". EMBO Journal, 20(23):6877-88.

Elbashir et al., (2001) "Duplexes of 21-nucleotide Mediated RNA Interference in Cultured Mammalian Cells". Nature 411:494-498.

Elmen et al. (2005) "Locked Nucleic Acid (LNA) Mediated Improvements in siRNA Stability and Functionality". NAR, 33(1):439-47.

Fire et al., (1998) "Potent and Specific Genetic Interference by Double-Stranded RNA in *Caenorhabditis elegans*". Nature, vol. 391:806-811.

Holen et al., (2002) "Positional Effects of Short Interfering RNAs Targeting the Human Coagulation Trigger Tissue Factor". NAR, 30(8):1757-66.

Kotlo, et al (2003) "Nrf2 is an inhibitor of the Fas pathway as identified by Achilles Heel Method, a new function-based approach to gene identification in human cells". Oncogene, 22: 797-806.

Mahato et al., (2005) "Modulation of Gene Expression by Antisense and Antigene Oligodeoxynucleotides and Small Interfering RNA". Expert Opinion on Drug Delivery, 2(1):3-28.

McManus et al., (2002) "Gene Silencing in Mammals by Small Interfering RNAs". Nature Reviews Genetics, vol. 3:737-747.

Prakash et al., (2005) "Positional Effect of Chemical Modifications on Short Interference RNA Activity in Mammalian Cells". J. Med Chem, 48(13)4247-53.

Scherer and Rossi (2004) "Therapeutic Applications of RNA Interferences: Recent Advances in siRNA Design". Advances in Genetics, 22:1-21.

Singh et al. (2008) "RNAi-Mediated Silencing of Nuclear Factor Erythroid-2-related Factor 2 Gene Expression in Non-Small Cell Lung Cancer Inhibits Tumor Growth and Increases Efficacy of Chemotherapy". Cancer Res. , 68(19) 7975-84.

Sioud et al . , (2004) "Potential Design Rules and Enzymatic Synthesis of siRNAs". Methods in Molec Biol. , 252 :457-468.

Ui-Tei at al . , (2006) "Essential Notes Regarding the Design of Functional siRNAs for Efficient Mammalian RNAi". J Biomed Biotechnol, 2006:65052.

Ui-Tei et al., (2008) "DNA-modified siRNA-dependent Gene Silencing with reduced Off-target Effect is Induced through a Pathway Parallel to that for siRNA-mediated RNA Interference". Proc 2008 Micro-NanoMechatronics and Human Science (MHS2008), 339-345.

Ui-Tei et al., (2008) "Functional Dissection of siRNA Sequence by Systematic DNA Substitution: Modified siRNA with a DNA Seed Arm is a Powerful Tool for Mammalian Gene Silencing with Significantly Reduced Off-target Effect". Nucleic Acids Research, 36 (7) :2136-51.

Urata et al., (1992) "Synthesis and Properties of Mirror-image DNA". Nucleic Acids Research, 20 (13) 3325-3332.

Zamore, et al., "RNAi: Double-Stranded RNA Directs the ATP-Dependent Cleavage of mRNA at 21 to 23 Nucleotide Intervals". Cell, (2000), 101:25-33.

Garbesi et al. (1993) "L-DNAs as Potential Antimessenger Oligonucleotides: A Reassessment". Nuc. Acids Res., 21 (18) :4159-65.

Kawakimi et al. (2005) "Thermodynamic Analysis of Duplex Formation of Heterochiral DNA with L-deoxyadenosine" . Analyt. Sci., Feb. 2005 (21): 77-82.

Kim et al. (2007) "Superior Structure Stability and Selectivity of Hairpin Nucleic Acid Probes with an L-DNA Stem". Nuc. Acids Res., 35 (21): 7279-7287.

Written Opinion issued by the International Searching Authority (ISA/US) on Jan. 8, 2009 in connection with International Application PCT/IL2008/000391 (WO 2008/114262).

International Preliminary Report on Patentability issued by the International Searching Authority (ISA/US) on Jan. 28, 2010 in connection with International Application PCT/IL2008/000391 (WO 2008/114262).

SIRNA COMPOUNDS FOR INHIBITING NRF2

This application is a §371 national stage of PCT International Application No. PCT/IL2009/000387, filed Apr. 6, 2009, and claims the benefit of U.S. Provisional Application Nos. 61/194,495, filed Sep. 25, 2008 and 61/124,196, filed Apr. 15, 2008, which are hereby incorporated by reference in their entirety.

This application incorporates-by-reference nucleotide and/or amino acid sequences which are present in the file named "101015_SubstituteSequenceListing_DES.txt," which is 2 megabytes in size, and which was created Oct. 15, 2010 in the IBM-PC machine format, having an operating system compatibility with MS-Windows, which is contained in the text file filed Oct. 15, 2010 as part of this application.

Throughout this application various patent and scientific publications are cited. The disclosures for these publications in their entireties are hereby incorporated by reference into this application to more fully describe the state of the art to which this invention pertains.

FIELD OF THE INVENTION

The present invention provides sense and antisense oligonucleotides useful in synthesis of chemically modified siRNA compounds that target the NRF2 gene (NFE2L2) and pharmaceutical compositions comprising same having utility in treating or preventing the incidence or severity of proliferative diseases, particularly lung cancers.

BACKGROUND OF THE INVENTION

The Nrf2 Gene and Polypeptide

Nuclear factor erythroid-2 related factor 2 (NFE2L2; Nrf2), a cap-and-collar basic leucine zipper transcription factor, positively regulates a transcriptional program that maintains cellular redox homeostasis and protects cells from oxidative insult, including insult from chemotherapeutic agents (Rangasamy, et al. 2004. J Clin Invest 114, 1248). Nrf2 activates transcription of its target genes through binding specifically to the antioxidant-response element (ARE) found in those genes' promoters. The Nrf2-regulated transcriptional program includes a broad spectrum of genes, including antioxidants such as heme oxygenase-1, superoxide dismutase, glutathione reductase (GSR), glutathione peroxidase, thioredoxin, thioredoxin reductase, and peroxiredoxins (PRDX).

Lung Cancer

Lung cancer usually develops in the cells lining the lung's air passages. The two main types are small cell lung cancer (SCLC) and non-small cell lung cancer (NSCLC), based on the cell morphology. In non-small cell lung cancer, results of standard treatment are poor except for the most localized cancers. Surgery is the most potentially curative therapeutic option for this disease; radiation therapy can produce a cure in only a small number of patients and can provide palliation in most patients. Adjuvant chemotherapy may provide an additional benefit to patients with resected NSCLC. In advanced-stage disease, chemotherapy offers modest improvements in median survival, though overall survival is poor. Chemotherapy has produced short-term improvement in disease-related symptoms. Other forms of lung cancer include metastases of a primary cancer.

PCT Patent Publication No. WO 2006/128041 discloses siRNA molecules for Nrf2 and their use in treating cancer, preferably lung and kidney cancers. US Patent Application Publication No. 20020164576 discloses a method of inhibiting tumor growth (preferably a lymphoma cancer) using antisense molecules directed to Nrf2 or specific antibodies. Co-assigned US Patent Application Publication No. 20070042418, discloses the use of Nrf2 inhibitors including siRNA molecules for treating cancer. Co-assigned PCT Patent Publication No. WO 2008/114262 discloses certain Nrf2 siRNA molecules.

siRNA and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defense mechanism which was activated in response to long dsRNA molecules (Gil et al. Apoptosis, 2000. 5:107-114). Later it was discovered that synthetic duplexes of 21 nucleotide RNAs could mediate gene specific RNAi in mammalian cells, without the stimulation of the generic antiviral defense mechanisms (see Elbashir et al. Nature 2001, 411:494-498 and Caplen et al. PNAS USA 2001, 98:9742-9747). As a result, small interfering RNAs (siRNAs), which are short double-stranded RNAs, have become powerful tools in attempting to understand gene function. Thus RNA interference (RNAi) refers to the process of sequence-specific post-transcriptional gene silencing in mammals mediated by small interfering RNAs (siRNAs) (Fire et al, Nature 1998. 391, 806) or microRNAs (miRNA; Ambros, Nature 2004 431: 7006, 350-55; and Bartel, Cell. 2004. 116(2):281-97). The corresponding process in plants is commonly referred to as specific posttranscriptional gene silencing or RNA silencing and is referred to as quelling in fungi.

A siRNA is a double-stranded RNA molecule which inhibits, either partially or fully, the expression of a gene/mRNA of its endogenous or cellular counterpart, or of an exogenous gene such as a viral nucleic acid. The mechanism of RNA interference is detailed infra.

Studies have revealed that siRNA is effective in vivo in mammals, including humans. Bitko et al., showed that specific siRNAs directed against the respiratory syncytial virus (RSV) nucleocapsid N gene are effective in treating mice when administered intranasally (Nat. Med. 2005, 11(1):50-55). For reviews of therapeutic applications of siRNAs see for example Barik (Mol. Med 2005, 83: 764-773) and Chakraborty (Current Drug Targets 2007 8(3):469-82). In addition, clinical studies with short siRNAs that target the VEGFR1 receptor in order to treat age-related macular degeneration (AMD) have been conducted in human patients (Kaiser, Am J Ophthalmol. 2006 142(4)660-8). Further information on the use of siRNA as therapeutic agents is available, see for example Durcan (Mol. Pharma. 2008. 5(4):559-566), Kim and Rossi (BioTechniques 2008. 44:613-616) and Grimm and Kay (JCI, 2007. 117(12):3633-41).

Chemically Modified siRNA

The selection and synthesis of siRNA corresponding to known genes has been widely reported (see for example Ui-Tei et al., 2006. J Biomed Biotechnol. 2006: 65052; Chalk et al., 2004. BBRC. 319(1): 264-74; Sioud & Leirdal, 2004. Met. Mol Biol. 252:457-69; Levenkova et al., 2004, Bioinform. 20(3):430-2; Ui-Tei et al., 2004. NAR 32(3):936-48).

Examples for the use of, and production of, chemically modified siRNA are found in Braasch et al., 2003. Biochem., 42(26):7967-75; Chiu et al., 2003, RNA, 9(9):1034-48; PCT Patent Publications Nos. WO 2004/015107 and WO 02/44321. U.S. Pat. Nos. 5,898,031 and 6,107,094 teach chemically modified oligomers. U.S. Pat. No. 7,452,987 relates to compounds having alternating unmodified and 2' sugar modified ribonucleotides. PCT Patent Application Nos. PCT/IL2008/000248 and PCT/IL2008/001197, assigned to the assignee of the present invention, and hereby incorporated by reference in their entirety, disclose chemically modified siRNA compounds.

Despite the evident progress, there remains a continued need for improved therapeutic molecules, in particular improved Nrf2 siRNA compounds, useful in treating cancerous or proliferative diseases, particularly lung cancers.

SUMMARY OF THE INVENTION

The present invention provides novel double stranded oligonucleotides that inhibit the Nrf2 gene. The invention also provides a pharmaceutical composition comprising one or more such oligonucleotides, and a vector capable of expressing the oligonucleotide. The present invention also relates to methods and compositions for treating or preventing the incidence or severity of a cancerous or proliferative disease, particularly various lung cancers. The methods and compositions involve administering to a mammal in need of such treatment a prophylactically or therapeutically effective amount of one or more oligonucleotide compounds which down-regulate the expression of the Nrf2 gene, particularly novel small interfering RNAs (siRNAs).

In one aspect the present invention provides novel siRNA compounds useful in inhibiting the NRF2 gene.

Accordingly, in one aspect the present invention provides a siRNA compound having the following structure:

5' (N)$_x$—Z 3' (antisense strand)
3' Z'—(N')$_y$-z" 5' (sense strand)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent, but if present is a capping moiety covalently attached at the 5' terminus of (N') y;

each of x and y is independently an integer between 18 and 40;

wherein the sequence of (N')y is substantially complementary to the sequence of (N)x; and wherein (N)x comprises an antisense sequence present in any one of Tables A-H (SEQ ID NOS: 4-8,533). In some embodiments the covalent bond joining each consecutive N or N' to the next N or N' is a phosphodiester bond. In some embodiments (N')y comprises two consecutive N' joined by a PACE bond at the 3' terminus.

In various embodiments x=y and each of x and y is 19, 20, 21, 22 or 23. In some embodiments x=y=19.

In some embodiments (N)x comprises at least five alternating unmodified and modified ribonucleotides beginning at the 3' end and at least nine modified ribonucleotides in total and each remaining N is an unmodified ribonucleotide. In some embodiments the modified ribonucleotide is a 2'-O-methyl (2'OMe) sugar modified ribonucleotide. In some embodiments (N)x comprises modified ribonucleotides in alternating positions wherein each N at the 5' and 3' termini are modified in their sugar residues and the middle ribonucleotide is an unmodified ribonucleotide, e.g. in position 10 in a 19-mer strand.

In various embodiments (N)x comprises 2'OMe sugar modified ribonucleotides at positions 1, 3, 5, 7, 9, 11, 13, 15, 17 and 19. In other embodiments, (N)x comprises 2'OMe sugar modified ribonucleotides at positions 2, 4, 6, 8, 11, 13, 15, 17 and 19.

In some embodiments (N')y comprises at least one mirror nucleotide, or a nucleotide joined to an adjacent nucleotide by a 2'-5' internucleotide phosphate bond.

In one embodiment of the above structure, the compound comprises at least one mirror nucleotide at one terminus or both termini in (N')y. In some embodiments the mirror nucleotide is selected from an L-ribonucleotide and an L-deoxyribonucleotide. In various embodiments the mirror nucleotide is an L-deoxyribonucleotide.

In various embodiments the compound comprises two consecutive mirror nucleotides, one at the 3' penultimate position and one at the 3' terminus in (N')y. In one preferred embodiment x=y=19 and (N')y comprises an L-deoxyribonucleotide at position 18.

In some embodiments y=19 and (N')y, consists of unmodified ribonucleotides at positions 1-17 and 19 and one L-DNA at the 3' penultimate position (position 18). In other embodiments y=19 and (N')y consists of unmodified ribonucleotides at position 1-16 and 19 and two consecutive L-DNA at the 3' penultimate position (positions 17 and 18).

In another embodiment of the above structure, (N')y comprises at least two consecutive nucleotide joined together to the next nucleotide by a 2'-5' phosphodiester bond at one or both termini. In certain preferred embodiments in (N')y the 3' penultimate nucleotide is linked to the 3' terminal nucleotide with a 2'-5' phosphodiester bridge.

In other embodiments of the above structures, (N')y further comprises one or more nucleotides containing a sugar moiety modified with an extra bridge at one or both termini. Non-limiting examples of such nucleotides, also referred to herein as bicyclic nucleotides, are locked nucleic acid (LNA) and ethylene-bridged nucleic acid (ENA).

In certain preferred embodiments the compound of the invention is a blunt-ended (z", Z and Z' are absent), double stranded oligonucleotide structure, wherein x=y=19, wherein (N')y comprises unmodified ribonucleotides in which three consecutive nucleotides at the 3' terminus are joined together by two 2'-5' phosphodiester bonds; and an antisense strand (AS) of alternating unmodified and 2'-O methyl sugar-modified ribonucleotides.

In some embodiments, neither (N)x nor (N')y are phosphorylated at the 3' and 5' termini. In other embodiments either or both (N)x and (N')y are phosphorylated at the 3' termini.

In some embodiments (N)x and its corresponding sense strand (N')y are selected from any one of the oligonucleotide pairs shown in Tables A-H, set forth in SEQ ID NOS: 4-8,533.

In certain embodiments the compound is blunt ended, for example wherein both Z and Z' are absent. In an alternative embodiment, the compound comprises at least one 3' overhang and/or a 5' capping moiety at the 5' terminus of (N')y, wherein at least one of Z or Z' or z" is present. Z, Z' and z" are independently one or more covalently linked modified or non-modified nucleotides, for example inverted dT or dA; dT, LNA, mirror nucleotide and the like. In some embodiments each of Z and Z' are independently selected from dT and dTdT. In certain specific embodiments Z and Z' are absent, z" is present and consists of inverted deoxyabasic moiety.

In a further aspect, the present invention provides a pharmaceutical composition comprising one or more compounds of the present invention, in an amount effective to inhibit target gene expression, and a pharmaceutically acceptable carrier wherein the target gene Nrf2.

Also provided by the present invention are methods and compositions for treating a patient suffering from a cancerous or proliferative disease, (e.g. lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. In one particular embodiment, the cancer is lung cancer including non-small-cell lung carcinoma (NSCLC) or small-cell lung carcinoma. The methods of the invention comprise administering to the patient one or more compounds which down-regulate the expression of the Nrf2 gene, particularly siRNAs that inhibit Nrf2, typically as a pharmaceutical composition, in a therapeutically effective dose so as to thereby treat the patient.

Still further, the invention relates to a method for treating or preventing the incidence or severity of a cancerous or proliferative disease, particularly a lung cancerous disease in a patient comprising administering to the patient a pharmaceutical composition comprising an effective amount of an siRNA molecule of the present invention; and a therapeutically acceptable carrier. Preferably, the siRNA is delivered as naked siRNA. In some embodiments the naked siRNA molecules are applied directly to the lung, for example via aerosol delivery, which has the potential for delivering high concentrations of the therapeutic molecule to the inner lung.

Still further, the invention relates to the use of a therapeutically effective dose of an oligonucleotide for the preparation of a composition for treating a subject suffering from a cancerous or proliferative disease, preferably lung cancer, wherein the oligonucleotide is present in any one of Tables A-H (SEQ ID NOS: 4-8,533).

In yet another aspect the present invention provides a method of sensitizing a cancer cell to a cancer therapy comprising contacting the cell with a double stranded compound according to the present invention wherein the double stranded compound inhibits expression of a Nrf2 polypeptide, thereby sensitizing the cell to the cancer therapy.

In some embodiments the cancer therapy is sleeted from a chemotherapeutic agent, and radiation therapy. In some embodiments the cancer cell is a lung cancer cell.

DETAILED DESCRIPTION OF THE INVENTION

The present invention relates generally to compounds which down-regulate expression of the Nrf2 gene, particularly to unmodified and chemically modified small interfering RNAs (siRNAs), and to the use of these novel siRNAs in the treatment of various diseases and medical conditions, in particular various forms of cancerous or proliferative diseases. Such preferred siRNA compounds comprise sense and corresponding antisense oligonucleotide sequences present in any one of Tables A-H (set forth as SEQ ID NOS: 4-8,533).

More preferred siRNA compounds comprise sense and corresponding antisense oligonucleotide sequences present in any one of Tables H1-H5 (set forth as SEQ ID NOS: 8,490-8,533). The sense and corresponding antisense oligonucleotide siRNA sequences present in Tables A-B (set forth as SEQ ID NOS:4-2,009) are disclosed in copending PCT application PCT/IL2008/000391 (WO2008/114262).

The inventors of the present invention provide novel siRNAs to Nrf2 having utility in treating or preventing any of the diseases or disorders disclosed herein and to pharmaceutical compositions comprising same.

The present invention further provides methods for inhibiting expression of a target Nrf2 gene in vivo. Without being bound to theory, the method includes administering an oligonucleotide, including a small interfering RNA (i.e., siRNA) that targets Nrf2 mRNA and hybridize to, or interacts with, the mRNA under physiological conditions, or a nucleic acid material that produces siRNA in a cell, in an amount sufficient to down-regulate expression of the Nrf2 gene. In some embodiments the Nrf2 gene is down regulated by an RNA interference mechanism. In particular, the subject method is used to inhibit expression of the Nrf2 gene for treatment or prevention of cancer or other disease in which expression of Nrf2 is a contraindication.

In accordance with the present invention, the Nrf2 inhibitors provided herein are used as drugs to treat various pathologies accompanied by an elevated level of Nrf2 polypeptide.

The present invention provides double-stranded oligoribonucleotides (siRNAs), which down-regulate the expression of the Nrf2 gene. In some embodiments the double-stranded oligoribonucleotides further comprises one or more deoxynucleotide, modified deoxynucleotide, modified ribonucleotide or unconventional moiety including a mirror deoxynucleotide. A siRNA of the present invention is a duplex oligoribonucleotide in which the sense strand is derived from the mRNA sequence of the Nrf2 gene, and the antisense strand is fully complementary or substantially complementary to the sense strand. In general, some deviation from the target mRNA sequence is tolerated without compromising the siRNA activity (see e.g. Czauderna et al 2003 Nucleic Acids Research 31(11), 2705-2716). Without being bound by theory, siRNA targets the mRNA for specific cleavage and degradation and/or may inhibit translation from the targeted message.

As used herein, the term "Nrf2 polypeptide" refers to the Nrf2 polypeptide (gi:20149576|ref|NP_006155) or to a homolog thereof having preferably 90% homology, more preferably 95% homology, and even more preferably 98% homology to the Nrf2 polypeptide as either full-length or a fragment or a domain thereof, as a mutant or the polypeptide encoded by a spliced variant nucleic acid sequence, as a chimera with other polypeptides, provided that any of the above has the same or substantially the same biological function as the Nrf2 polypeptide.

As used herein, the term "Nrf2", "Nrf2 mRNA", "Nrf2 gene", "Nrf2 polynucleotide" (gi|166295208|ref|NM_006164.3| Homo sapiens nuclear factor (erythroid-derived 2)-like 2 (NFE2L2)) SEQ ID NOS: 1-3 is defined as any homolog of the Nrf2 polynucleotide having preferably 90% homology, more preferably 95% homology, and even more preferably 98% homology to the Nrf2 mRNA, as either full-length or a fragment or a domain thereof, or as a mutant of the polynucleotide.

siRNA and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defense mechanism which was activated in response to long dsRNA molecules (Gil et al. Apoptosis, 2000. 5:107-114). Later it was discovered that synthetic duplexes of 21 nucleotide RNAs could mediate gene specific RNAi in mammalian cells, without the stimulation of the generic antiviral defense mechanisms (see Elbashir et al. Nature 2001, 411:494-498 and Caplen et al. PNAS USA 2001, 98:9742-9747). As a result, small interfering RNAs (siRNAs), which are short double-stranded RNAs, have become powerful tools in attempting to understand gene function. Thus RNA interference (RNAi) refers to the process of sequence-specific post-transcriptional gene silencing in mammals mediated by small interfering RNAs (siRNAs) (Fire et al, Nature 1998. 391, 806) or microRNAs (miRNA; Ambros, Nature 2004 431: 7006, 350-55; and Bartel, Cell. 2004. 116(2):281-97). The corresponding process in plants is commonly referred to as specific post transcriptional gene silencing or RNA silencing and in fungi is referred to as quelling.

A siRNA is a double-stranded RNA molecule which inhibits, either partially or fully, the expression of a gene/mRNA of its endogenous or cellular counterpart, or of an exogenous gene such as a viral nucleic acid.

siRNA has recently been successfully used for inhibition in primates (Tolentino et al., Retina 2004. 24(1):132-138). Several studies have revealed that siRNA therapeutics are effective in vivo in both mammals and in humans. Bitko et al., have shown that specific siRNA molecules directed against the respiratory syncytial virus (RSV) nucleocapsid N gene are effective in treating mice when administered intranasally (Bitko et al., Nat. Med. 2005, 11(1):50-55). For a review of the use of siRNA as therapeutics, see Barik (J. Mol. Med. 2005. 83: 764-773) and Dykxhoorn, et al (Gene Therapy 2006, 13, 541-552). siRNA oligonucleotides Tables A-H provide nucleic acid sequences of sense and corresponding antisense oligonucleotides, useful in preparing unmodified and chemically modified siRNA compounds of the invention. Antisense and corresponding sense oligonucleotides useful in preparing siRNA according to the present invention are set forth in Tables A-H (SEQ ID NOS: 4-8,533). Throughout the specification, nucleotide positions are numbered from 1 to 19 or 1 to 21 or 1 to 23 and are counted from the 5' end of the antisense or sense oligonucleotides. For example, position 1 on (N)x refers to the 5' terminal nucleotide on the antisense oligonucleotide strand.

According to the present invention the siRNA compounds are chemically and or structurally modified according to one of the following modifications set forth in Structures (A)-(P) or as tandem siRNA or RNAstar.

In one aspect the present invention provides a compound set forth as Structure (A):

(A) 5' $(N)_x$—Z 3' (antisense strand)
3' Z'—$(N')_y$ 5' (sense strand)

wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein each of x and y is an integer between 18 and 40;

wherein each of Z and Z' may be present or absent, but if present is 1-5 consecutive nucleotides covalently attached at the 3' terminus of the strand in which it is present;

wherein the sequence of $(N')_y$ is a sequence substantially complementary to (N)x; and wherein the sequence of $(N)_x$ comprises an antisense sequence substantially identical to an antisense sequence set forth in any one of Tables C-H (SEQ ID NOS: 2010-8,533).

In certain embodiments the present invention provides a compound having structure (B):

(B) 5' (N)x-Z 3' antisense strand
3' Z—'(N')y 5' sense strand wherein each of $(N)_x$ and $(N')_y$ is an oligomer in which each consecutive N or N' is an unmodified ribonucleotide or a modified ribonucleotide joined to the next N or N' by a covalent bond;

wherein each of Z and Z' may be present or absent, but if present is 1-5 consecutive nucleotides covalently attached at the 3' terminus of the strand in which it is present;

wherein each of x and y=19, 21 or 23 and $(N)_x$ and $(N')_y$ are fully complementary wherein alternating ribonucleotides in each of $(N)_x$ and $(N')_y$ are modified to result in a 2'-O-methyl (2'OMe) modification in the sugar residue of the ribonucleotides;

wherein the sequence of $(N')_y$ is a sequence substantially complementary to (N)x; and wherein the sequence of $(N)_x$ comprises an antisense sequence substantially identical to an antisense sequence set forth in any one of Tables C-H (SEQ ID NOS: 2010-8,533).

In some embodiments each of $(N)_x$ and $(N')_y$ is independently phosphorylated or non-phosphorylated at the 3' and 5' termini.

In certain embodiments wherein each of x and y=19 or 23, each N at the 5' and 3' termini of $(N)_x$ is modified; and each N' at the 5' and 3' termini of $(N')_y$ is unmodified.

In certain embodiments wherein each of x and y=21, each N at the 5' and 3' termini of $(N)_x$ is unmodified; and each N' at the 5' and 3' termini of $(N')_y$ is modified.

In particular embodiments, when x and y=19, the siRNA is modified such that a 2'OMe group is present on the first, third, fifth, seventh, ninth, eleventh, thirteenth, fifteenth, seventeenth and nineteenth nucleotide of the antisense strand $(N)_x$, and whereby the very same modification, i.e. a 2'OMe group, is present at the second, fourth, sixth, eighth, tenth, twelfth, fourteenth, sixteenth and eighteenth nucleotide of the sense strand $(N')_y$. In various embodiments these particular siRNA compounds are blunt ended at both termini.

In some embodiments, the present invention provides a compound having Structure (C):

(C) 5' (N)x-Z 3' antisense strand
3' Z'—(N')y 5' sense strand wherein each of N and N' is a nucleotide independently selected from an unmodified ribonucleotide, a modified ribonucleotide, an unmodified deoxyribonucleotide and a modified deoxyribonucleotide;

wherein each of (N)x and (N')y is an oligomer in which each consecutive nucleotide is joined to the next nucleotide by a covalent bond and each of x and y is an integer between 18 and 40;

wherein in (N)x the nucleotides are unmodified or (N)x comprises alternating 2'OMe modified ribonucleotides and unmodified ribonucleotides; and the ribonucleotide located at the middle position of (N)x is 2'OMe modified or unmodified, preferably unmodified;

wherein (N')y comprises unmodified ribonucleotides further comprising one modified nucleotide at a terminal or penultimate position, wherein the modified nucleotide is selected from the group consisting of a mirror nucleotide, a bicyclic nucleotide, a 2'-sugar modified nucleotide, an altritol nucleotide, or a nucleotide joined to an adjacent nucleotide by an internucleotide linkage selected from a 2'-5' phosphodiester bond, a P-alkoxy linkage or a PACE linkage;

wherein if more than one nucleotide is modified in (N')y, the modified nucleotides may be consecutive;

wherein each of Z and Z' may be present or absent, but if present is 1-5 deoxyribonucleotides covalently attached at the 3' terminus of any oligomer to which it is attached;

wherein the sequence of $(N')_y$ comprises a sequence substantially complementary to (N)x; and wherein the sequence of $(N)_x$ comprises an antisense sequence substantially complementary to about 18 to about 40 consecutive ribonucleotides in an mRNA set forth in any one of SEQ ID NOS:1-3. Preferably $(N)_x$ comprises an antisense sequence substantially identical to an antisense sequence set forth in any one of Tables A-H (SEQ ID NOS: 4-8,533).

In particular embodiments, x=y=19 and in (N)x each modified ribonucleotide is modified so as to have a 2'-O-methyl on its sugar and the ribonucleotide located at the middle of (N)x is unmodified. Accordingly, in a compound wherein x=19, (N)x comprises 2'-O-methyl sugar modified ribonucleotides at positions 1, 3, 5, 7, 9, 11, 13, 15, 17 and 19. In other embodiments, (N)x comprises 2'OMe modified ribonucleotides at positions 2, 4, 6, 8, 11, 13, 15, 17 and 19 and may further comprise at least one abasic or inverted abasic unconventional moiety for example in position 5. In other embodiments, (N)x comprises 2'OMe modified ribonucleotides at positions 2, 4, 8, 11, 13, 15, 17 and 19 and may further comprise at least one abasic or inverted abasic unconventional moiety for example in position 6. In other embodiments, (N)x comprises 2'OMe modified ribonucleotides at positions 2, 4, 6, 8, 11, 13, 17 and 19 and may further comprise at least one abasic or inverted abasic unconventional moiety for example in position 15. In other embodiments, (N)x comprises 2'OMe modified ribonucleotides at positions 2, 4, 6, 8, 11, 13, 15, 17 and 19 and may further comprise at least one abasic or inverted abasic unconventional moiety for example in position 14. In other embodiments, (N)x comprises 2'OMe modified ribonucleotides at positions 1, 2, 3, 7, 9, 11, 13, 15, 17 and 19 and may further comprise at least one abasic or inverted abasic unconventional moiety for example in position 5. In other embodiments, (N)x comprises 2'OMe modified ribonucleotides at positions 1, 2, 3, 5, 7, 9, 11, 13, 15, 17 and 19 and may further comprise at least one abasic or inverted abasic unconventional moiety for example in position 6. In other embodiments, (N)x comprises 2'OMe modified ribonucleotides at positions 1, 2, 3, 5, 7, 9, 11, 13, 17 and 19 and may further comprise at least one abasic or inverted abasic unconventional moiety for example in position 15. In other embodiments, (N)x comprises 2'OMe modified ribonucleotides at positions 1, 2, 3, 5, 7, 9, 11, 13, 15, 17 and 19 and may further comprise at least one abasic or inverted abasic unconventional moiety for example in position 14. In other embodiments, (N)x comprises 2'OMe modified ribonucleotides at positions 2, 4, 6, 7, 9, 11, 13, 15, 17 and 19 and may further comprise at least one abasic or inverted abasic unconventional moiety for example in position 5. In other embodiments, (N)x comprises 2'OMe modified ribonucleotides at positions 1, 2, 4, 6, 7, 9, 11, 13, 15, 17 and 19 and may further comprise at least one abasic or inverted abasic unconventional moiety for example in position 5. In other embodiments, (N)x comprises 2'OMe modified ribonucleotides at positions 2, 4, 6, 8, 11, 13, 14, 16, 17 and 19 and may further comprise at least one abasic or inverted abasic unconventional moiety for example in position 15. In other embodiments, (N)x comprises 2'OMe modified ribonucleotides at positions 1, 2, 3, 5, 7, 9, 11, 13, 14, 16, 17 and 19 and may further comprise at least one abasic or inverted abasic unconventional moiety for example in position 15. In other embodiments, (N)x comprises 2'OMe modified ribonucleotides at positions 2, 4, 6, 8, 11, 13, 15, 17 and 19 and may further comprise at least one abasic or inverted abasic unconventional moiety for example in position 7. In other embodiments, (N)x comprises 2'O-Me modified ribonucleotides at positions 2, 4, 6, 11, 13, 15, 17 and 19 and may further comprise at least one abasic or inverted abasic unconventional moiety for example in position 8. In other embodiments, (N)x comprises 2'OMe modified ribonucleotides at positions 2, 4, 6, 8, 11, 13, 15, 17 and 19 and may further comprise at least one abasic or inverted abasic unconventional moiety for example in position 9. In other embodiments, (N)x comprises 2'OMe modified ribonucleotides at positions 2, 4, 6, 8, 11, 13, 15, 17 and 19 and may further comprise at least one abasic or inverted abasic unconventional moiety for example in position 10. In other embodiments, (N)x comprises 2'OMe modified ribonucleotides at positions 2, 4, 6, 8, 13, 15, 17 and 19 and may further comprise at least one abasic or inverted abasic unconventional moiety for example in position 11. In other embodiments, (N)x comprises 2'OMe modified ribonucleotides at positions 2, 4, 6, 8, 11, 13, 15, 17 and 19 and may further comprise at least one abasic or inverted abasic unconventional moiety for example in position 12. In other embodiments, (N)x comprises 2'O-Me modified ribonucleotides at positions 2, 4, 6, 8, 11, 15, 17 and 19 and may further comprise at least one abasic or inverted abasic unconventional moiety for example in position 13.

In yet other embodiments (N)x comprises at least one nucleotide mismatch relative to one of the mRNA disclosed herein, and particularly the mRNA transcribed from the mammalian genes of Table 3. In certain preferred embodiments, (N)x comprises a single nucleotide mismatch on position 5, 6, or 14. In one embodiment of Structure (C), at least two nucleotides at either or both the 5' and 3' termini of (N')y are joined by a 2'-5' phosphodiester bond. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and three nucleotides at the 3' terminus of (N')y are joined by two 2'-5' phosphodiester bonds (set forth herein as Structure I). In other preferred embodiments, x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N')y may be modified with 2'OMe on its sugar. In another preferred embodiment, in (N)x the nucleotides alternate between 2'OMe modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-methyl modifications.

In certain preferred embodiments of Structure C, x=y=19 and in (N')y, at least one position comprises an abasic or inverted abasic unconventional moiety, preferably five positions comprises an abasic or inverted abasic unconventional moieties. In various embodiments, the following positions comprise an abasic or inverted abasic: positions 1 and 16-19, positions 15-19, positions 1-2 and 17-19, positions 1-3 and 18-19, positions 1-4 and 19 and positions 1-5. (N')y may further comprise at least one LNA nucleotide.

In certain preferred embodiments of Structure C, x=y=19 and in (N')y the nucleotide in at least one position comprises a mirror nucleotide, a deoxyribonucleotide and a nucleotide joined to an adjacent nucleotide by a 2'-5' internucleotide bond.

In certain preferred embodiments of Structure C, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. In certain embodiments (N')y further comprises a 5' terminal cap nucleotide such as 5'-O-methyl DNA or an abasic or inverted abasic moiety as an overhang.

In yet other embodiments (N')y comprises a DNA at position 15 and L-DNA at one or both of positions 17 and 18. In that structure, position 2 may further comprise an L-DNA or an abasic unconventional moiety.

Other embodiments of Structure C are envisaged wherein x=y=21 in these embodiments the modifications for (N')y discussed above instead of being on positions 15, 16, 17, 18 are on positions 17, 18, 19, 20 for 21-mer.; similarly the modifications at one or both of positions 17 and 18 are on one or both of positions 19 or 20 for the 21-mer. All modifications in the 19-mer are similarly adjusted for the 21- and 23-mer.

According to various embodiments of Structure (C), in (N')y 2, 3, 4, 5, 6, 7, 8, 9, 10, 11, 12, 13 or 14 consecutive ribonucleotides at the 3' terminus are linked by 2'-5' internucleotide linkages In one preferred embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'OMe sugar modification. In certain preferred embodiments of Structure C, x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16-17, 17-18, or 16-18 in (N')y are joined by a 2'-5' internucleotide bond.

In certain embodiments (N')y comprises an L-DNA at position 2 and 2'-5' internucleotide bonds at positions 16-17, 17-18, or 16-18. In certain embodiments (N')y comprises 2'-5' internucleotide bonds at positions 16-17, 17-18, or 16-18 and a 5' terminal cap nucleotide.

According to various embodiments of Structure (C), in (N')y 2, 3, 4, 5, 6, 7, 8, 9, 10, 11, 12, 13 or 14 consecutive nucleotides at either terminus or 2-8 modified nucleotides at each of the 5' and 3' termini are independently mirror nucleotides. In some embodiments the mirror nucleotide is an L-ribonucleotide. In other embodiments the mirror nucleotide is an L-deoxyribonucleotide. The mirror nucleotide may further be modified at the sugar or base moiety or in an internucleotide linkage.

In one preferred embodiment of Structure (C), the 3' terminal nucleotide or two or three consecutive nucleotides at the 3' terminus of (N')y are L-deoxyribonucleotides.

In other embodiments of Structure (C), in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'OMe). In one series of preferred embodiments, three, four or five consecutive nucleotides at the 5' terminus of (N')y comprise the 2'OMe modification. In another preferred embodiment, three consecutive nucleotides at the 3' terminus of (N')y comprise the 2'OMe modification.

In some embodiments of Structure (C), in (N')y 2, 3, 4, 5, 6, 7, 8, 9, 10, 11, 12, 13 or 14 consecutive ribonucleotides at either or 2-8 modified nucleotides at each of the 5' and 3' termini are independently bicyclic nucleotides. In various embodiments the bicyclic nucleotide is a locked nucleic acid (LNA) or a species of LNA, e.g. 2'-O, 4'-C-ethylene-bridged nucleic acid (ENA) is a species of LNA.

In various embodiments (N')y comprises modified nucleotides at the 5' terminus or at both the 3' and 5' termini.

In some embodiments of Structure (C), at least two nucleotides at either or both the 5' and 3' termini of (N')y are joined by P-ethoxy backbone modifications. In certain preferred embodiments x=y=19 or x=y=23; in (N)x the nucleotides alternate between modified ribonucleotides and unmodified ribonucleotides, each modified ribonucleotide being modified so as to have a 2'OMe on its sugar and the ribonucleotide located at the middle position of (N)x being unmodified; and four consecutive nucleotides at the 3' terminus or at the 5' terminus of (N')y are joined by three P-ethoxy backbone modifications. In another preferred embodiment, three consecutive nucleotides at the 3' terminus or at the 5' terminus of (N')y are joined by two P-ethoxy backbone modifications.

In some embodiments of Structure (C), in (N')y 2, 3, 4, 5, 6, 7 or 8, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one preferred embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one specific embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being modified so as to have a 2'OMe on its sugar and the ribonucleotide located at the middle of (N)x being unmodified, or the ribonucleotides in (N)x being unmodified.

In another embodiment of Structure (C), the present invention provides a compound wherein x=y=19 or x=y=23; in (N)x the nucleotides alternate between modified ribonucleotides and unmodified ribonucleotides, each modified ribonucleotide being modified so as to have a 2'OMe on its sugar and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA.

In another embodiment of Structure (C), five consecutive nucleotides at the 5' terminus of (N')y comprise the 2'OMe sugar modification and two consecutive nucleotides at the 3' terminus of (N')y are L-DNA.

In yet another embodiment, the present invention provides a compound wherein x=y=19 or x=y=23; (N)x consists of unmodified ribonucleotides; three consecutive nucleotides at the 3' terminus of (N')y are joined by two 2'-5' phosphodiester bonds and three consecutive nucleotides at the 5' terminus of (N')y are LNA such as ENA.

According to other embodiments of Structure (C), in (N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some preferred embodiments in (N')y, 1 or 2 consecutive nucleotides at each of the 5' and 3' termini are PACE nucleotides.

In additional embodiments, the present invention provides a compound having Structure (D): (D) 5' (N)x-Z 3' antisense strand 3' Z'—(N')y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is independently an integer between 18 and 40;

wherein (N)x comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence substantially complementary to about 18 to about 40 consecutive ribonucleotides in an mRNA set forth in any one of SEQ ID NOS:1-3. Preferably $(N)_x$ comprises an antisense sequence substantially identical to an antisense sequence set forth in any one of Tables A-H (SEQ ID NOS: 4-8,533).

In one embodiment of Structure (D), x=y=19 or x=y=23; (N)x comprises unmodified ribonucleotides in which two consecutive nucleotides linked by one 2'-5' internucleotide linkage at the 3' terminus; and (N')y comprises unmodified ribonucleotides in which two consecutive nucleotides are linked by one 2'-5' internucleotide linkage at the 5' terminus.

In some embodiments, x=y=19 or x=y=23; (N)x comprises unmodified ribonucleotides in which three consecutive nucleotides at the 3' terminus are joined together by two 2'-5' phosphodiester bonds; and (N')y comprises unmodified ribonucleotides in which four consecutive nucleotides at the 5' terminus are joined together by three 2'-5' phosphodiester bonds (set forth herein as Structure II).

According to various embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are linked by 2'-5' internucleotide linkages.

According to one preferred embodiment of Structure (D), four consecutive nucleotides at the 5' terminus of (N')y are joined by three 2'-5' phosphodiester bonds and three consecutive nucleotides at the 3' terminus of (N')x are joined by two 2'-5' phosphodiester bonds. Three nucleotides at the 5' terminus of (N')y and two nucleotides at the 3' terminus of (N')x may also comprise 3'-O-methyl modifications.

According to various embodiments of Structure (D), 2, 3, 4, 5, 6, 7, 8, 9, 10, 11, 12, 13 or 14 consecutive nucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently mirror nucleotides. In some embodiments the mirror is an L-ribonucleotide. In other embodiments the mirror nucleotide is L-deoxyribonucleotide.

In other embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently 2' sugar modified nucleotides. In some embodiments the 2' sugar modification comprises an amino, a fluoro, an alkoxy or an alkyl moiety. In certain embodiments the 2' sugar modification comprises a methoxy moiety (2'OMe).

In one preferred embodiment of Structure (D), five consecutive nucleotides at the 5' terminus of (N')y comprise the 2'OMe modification and five consecutive nucleotides at the 3' terminus of (N')x comprise the 2'OMe modification. In another preferred embodiment of Structure (D), ten consecutive nucleotides at the 5' terminus of (N')y comprise the 2'OMe modification and five consecutive nucleotides at the 3' terminus of (N')x comprise the 2'OMe modification. In another preferred embodiment of Structure (D), thirteen consecutive nucleotides at the 5' terminus of (N')y comprise the 2'OMe modification and five consecutive nucleotides at the 3' terminus of (N')x comprise the 2'OMe modification.

In some embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (D), (N')y comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In various embodiments of Structure (D), (N)x comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In some embodiments wherein each of the 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In one specific embodiment of Structure (D), five consecutive nucleotides at the 5' terminus of (N')y comprise the 2'OMe modification and two consecutive nucleotides at the 3' terminus of (N')y are L-DNA. In addition, the compound may further comprise five consecutive 2'OMe modified nucleotides at the 3' terminus of (N')x.

In various embodiments of Structure (D), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (E): (E) 5' (N)x-Z 3' antisense strand 3' Z'—(N')y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is independently an integer between 18 and 40;

wherein (N)x comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of (N')$_y$ is a sequence substantially complementary to (N)x; and wherein the sequence of (N)$_x$ comprises an antisense sequence substantially complementary to about 18 to about 40 consecutive ribonucleotides in an mRNA set forth in any one of SEQ ID NOS:1-3. Preferably (N)$_x$ comprises an antisense sequence substantially identical to an antisense sequence set forth in any one of Tables A-H (SEQ ID NOS: 4-8,533).

In certain preferred embodiments the ultimate nucleotide at the 5' terminus of (N)x is unmodified.

According to various embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are linked by 2'-5' internucleotide linkages.

According to various embodiments of Structure (E), 2, 3, 4, 5, 6, 7, 8, 9, 10, 11, 12, 13 or 14 consecutive nucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive nucleotides starting at the ultimate or penultimate position of the 3' terminus of (N')y are independently mirror nucleotides. In some embodiments the mirror is an L-ribonucleotide. In other embodiments the mirror nucleotide is L-deoxyribonucleotide.

In other embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently 2' sugar modified nucleotides. In some embodiments the 2' sugar modification comprises an amino, a fluoro, an alkoxy or an alkyl moiety. In certain embodiments the 2' sugar modification comprises a methoxy moiety (2'OMe).

In some embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably stalling at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (E), (N')y comprises modified nucleotides selected from a bicyclic nucleotide, a 2' sugar modified nucleotide, a mirror nucleotide, an altritol nucleotide, a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In various embodiments of Structure (E), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where both 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (E), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (F): (F) 5' (N)x-Z 3' antisense strand 3' Z'—(N')y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is independently an integer between 18 and 40;

wherein each of (N)x and (N')y comprise unmodified ribonucleotides in which each of (N)x and (N')y independently comprise one modified nucleotide at the 3' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a PACE linkage or a nucleotide joined to an adjacent nucleotide by a 2'-5' phosphodiester bond;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of (N')y is a sequence substantially complementary to (N)x; and wherein the sequence of (N)$_x$ comprises an antisense sequence substantially complementary to about 18 to about 40 consecutive ribonucleotides in an mRNA set forth in any one of SEQ ID NOS:1-3. Preferably (N)$_x$ comprises an antisense sequence substantially identical to an antisense sequence set forth in any one of Tables A-H (SEQ ID NOS: 4-8,533).

In some embodiments of Structure (F), x=y=19 or x=y=23; (N')y comprises unmodified ribonucleotides in which two consecutive nucleotides at the 3' terminus comprise two consecutive mirror deoxyribonucleotides; and (N)x comprises unmodified ribonucleotides in which one nucleotide at the 3' terminus comprises a minor deoxyribonucleotide (set forth as Structure III).

According to various embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are linked by 2'-5' internucleotide linkages.

According to one preferred embodiment of Structure (F), three consecutive nucleotides at the 3' terminus of (N')y are joined by two 2'-5' phosphodiester bonds and three consecutive nucleotides at the 3' terminus of (N')x are joined by two 2'-5' phosphodiester bonds.

According to various embodiments of Structure (F), 2, 4, 5, 6, 7, 8, 9, 10, 11, 12, 13 or 14 consecutive nucleotides independently beginning at the ultimate or penultimate position of the 3' termini of (N)x and (N')y are independently minor nucleotides. In some embodiments the mirror nucleotide is an L-ribonucleotide. In other embodiments the mirror nucleotide is an L-deoxyribonucleotide.

In other embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently 2' sugar modified nucleotides. In some embodiments the 2' sugar modification comprises an amino, a fluoro, an alkoxy or an alkyl moiety. In certain embodiments the 2' sugar modification comprises a methoxy moiety (2'OMe).

In some embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (F), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at both the 3' and 5' termini.

In various embodiments of Structure (F), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (F), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (G): (G) 5' (N)x-Z 3' antisense strand 3' Z'—(N')y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is independently an integer between 18 and 40;

wherein each of (N)x and (N')y comprise unmodified ribonucleotides in which each of (N)x and (N')y independently comprise one modified nucleotide at the 5' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a PACE linkage or a nucleotide joined to an adjacent nucleotide by a 2'-5' phosphodiester bond;

wherein for (N)x the modified nucleotide is preferably at penultimate position of the 5' terminal;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of (N')$_y$ is a sequence substantially complementary to (N)x; and wherein the sequence of (N)$_x$ comprises an antisense sequence substantially complementary to about 18 to about 40 consecutive ribonucleotides in an mRNA set forth in any one of SEQ ID NOS:1-3. Preferably (N)$_x$ comprises an antisense sequence substantially identical to an antisense sequence set forth in any one of Tables A-H (SEQ ID NOS: 4-8,533).

In some embodiments of Structure (G), x=y=19 or x=y=23.

According to various embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are linked by 2'-5' internucleotide linkages. For (N)x the modified nucleotides preferably start at the penultimate position of the 5' terminal.

According to various embodiments of Structure (G), 2, 3, 4, 5, 6, 7, 8, 9, 10, 11, 12, 13 or 14 consecutive nucleotides independently beginning at the ultimate or penultimate position of the 5' termini of (N)x and (N')y are independently mirror nucleotides. In some embodiments the mirror nucleotide is an L-ribonucleotide. In other embodiments the mirror nucleotide is an L-deoxyribonucleotide. For (N)x the modified nucleotides preferably start at the penultimate position of the 5' terminal.

In other embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are independently 2' sugar modified nucleotides. In some embodiments the 2' sugar modification comprises an amino, a fluoro, an alkoxy or an alkyl moiety. In certain embodiments the 2' sugar modification comprises a methoxy moiety (2'OMe). In some preferred embodiments the consecutive modified nucleotides preferably begin at the penultimate position of the 5' terminus of (N)x.

In one preferred embodiment of Structure (G), five consecutive ribonucleotides at the 5' terminus of (N')y comprise a 2'OMe modification and one ribonucleotide at the 5' penultimate position of (N')x comprises a 2'OMe modification. In another preferred embodiment of Structure (G), five consecutive ribonucleotides at the 5' terminus of (N')y comprise a 2'OMe modification and two consecutive ribonucleotides at the 5' terminal position of (N')x comprise a 2'OMe modification.

In some embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are bicyclic nucleotides. In various embodiments the bicyclic nucleotide is a locked nucleic acid (LNA) such as a 2'-O, 4'-C-ethylene-bridged nucleic acid (ENA). In some preferred embodiments the consecutive modified nucleotides preferably begin at the penultimate position of the 5' terminus of (N)x.

In various embodiments of Structure (G), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In various embodiments of Structure (G), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond. In various embodiments of Structure (G), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (H): (H) 5' (N)x-Z 3' antisense strand 3' Z'—(N)y 5' sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is independently an integer between 18 and 40;

wherein (N)x comprises unmodified ribonucleotides further comprising one modified nucleotide at the 3' terminal or penultimate position or the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at an internal position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of (N')y is a sequence substantially complementary to (N)x; and wherein the sequence of (N)x comprises an antisense sequence substantially complementary to about 18 to about 40 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533).

In one embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or both termini of (N)x are independently 2' sugar modified nucleotides, bicyclic nucleotides, mirror nucleotides, altritol nucleotides or nucleotides joined to an adjacent nucleotide by a 2'-5' phosphodiester bond and 2, 3, 4, 5, 6, 7, 8, 9, 10, 11, 12, 13 or 14 consecutive internal ribonucleotides in (N')y are independently 2' sugar modified nucleotides, bicyclic nucleotides, mirror nucleotides, altritol nucleotides or nucleotides joined to an adjacent nucleotide by a 2'-5' phosphodiester bond. In some embodiments the 2' sugar modification comprises an amino, a fluoro, an alkoxy or an alkyl moiety. In certain embodiments the 2' sugar modification comprises a methoxy moiety (2'OMe).

In another embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or 2-8 consecutive nucleotides at each of 5' and 3' termini of (N')y are independently 2' sugar modified nucleotides, bicyclic nucleotides, mirror nucleotides, altritol nucleotides or nucleotides joined to an adjacent nucleotide by a 2'-5' phosphodiester bond, and 2, 3, 4, 5, 6, 7, 8, 9, 10, 11, 12, 13 or 14 consecutive internal ribonucleotides in (N)x are independently 2' sugar modified nucleotides, bicyclic nucleotides, mirror nucleotides, altritol nucleotides or nucleotides joined to an adjacent nucleotide by a phosphodiester bond.

In one embodiment wherein each of 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (H), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In one preferred embodiment of Structure (H), x=y=19; three consecutive ribonucleotides at the 9-11 nucleotide positions of (N')y comprise 2'OMe modification and five consecutive ribonucleotides at the 3' terminal position of (N')x comprise 2'OMe modification.

For all the above Structures (A)-(H), in various embodiments x=y and each of x and y is and integer selected from the group consisting of 19, 20, 21, 22 and 23. In certain embodiments, x=y=19. In other embodiments x=y=21. In additional embodiments the compounds of the invention comprise modified ribonucleotides in alternating positions wherein each N at the 5' and 3' termini of (N)x is modified in its sugar residue and the middle ribonucleotide is not modified, e.g. ribonucleotide in position 10 in a 19-mer strand, position 11 in a 21-mer and position 12 in a 23-mer strand.

In some embodiments where x=y=21 or x=y=23 the position of modifications in the 19-mer are adjusted for a 21- or 23-mer oligonucleotide with the proviso that the middle nucleotide of the antisense strand is preferably not modified.

In some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 5' termini position using cleavable or non-cleavable phosphate groups. In some embodiments the siRNA compounds are blunt ended and are non-phosphorylated at the termini; however, comparative experiments have shown that siRNA compounds phosphorylated at one or both of the 3'-termini have similar activity in vivo compared to the non-phosphorylated compounds.

In certain embodiments for all the above-mentioned Structures, the siRNA compound is blunt ended, for example wherein both Z and Z' are absent. In an alternative embodiment, the compound comprises at least one 3' overhang, wherein at least one of Z or Z' is present. Z and Z' independently comprises one or more covalently linked modified or non-modified nucleotides, for example inverted dT or dA; dT, LNA, mirror nucleotide and the like. In some embodiments each of Z and Z' are independently selected from dT and dTdT. siRNA in which Z and/or Z' is present have similar activity and stability as siRNA in which Z and Z' are absent.

In certain embodiments for all the above-mentioned Structures, the siRNA compound comprises one or more phosphonocarboxylate and/or phosphinocarboxylate nucleotides (PACE nucleotides). In some embodiments the PACE nucleotides are deoxyribonucleotides and the phosphinocarboxylate nucleotides are phosphinoacetate nucleotides.

In certain embodiments for all the above-mentioned Structures, the siRNA compound comprises one or inure locked nucleic acids (LNA) also defined as bridged nucleic acids or bicyclic nucleotides. Preferred locked nucleic acids are 2'-O, 4'-C-ethylene nucleosides (ENA) or 2'-O, 4'C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allart, et al., 1998. Nucleosides & Nucleotides 17:1523-1526; Herdewijn et al., 1999. Nucleosides & Nucleotides 18:1371-1376; Fisher et al., 2007, NAR 35(4):1064-1074; all incorporated herein by reference).

The present invention explicitly excludes compounds in which each of N and/or N' is a deoxyribonucleotide (D-A, D-C, D-G, D-T). In certain embodiments (N)x and (N')y may comprise independently 1, 2, 3, 4, 5, 6, 7, 8, 9 or more deoxyribonucleotides. In certain embodiments the present invention provides a compound wherein each of N is an unmodified ribonucleotide and the 3' terminal nucleotide or 2, 3, 4, 5, 6, 7, 8, 9, 10, 11, 12, 13 or 14 consecutive nucleotides at the 3' terminus of (N')y are deoxyribonucleotides. In yet other embodiments each of N is an unmodified ribonucleotide and the 5' terminal nucleotide or 2, 3, 4, 5, 6, 7, 8, 9, 10, 11, 12, 13 or 14 consecutive nucleotides at the 5' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide, In certain embodiments the 3' terminal nucleotide or 2, 3, 4, 5, 6, 7, 8, 9, 10, 11, 12 13 or 14 consecutive nucleotides at the 3' terminus of (N')y and the terminal 5' nucleotide or 2, 3, 4, 5, 6, 7, 8, 9, 10, 11, 12, 13 or 14 consecutive nucleotides at the 5' terminus of (N)x are deoxyribonucleotides. The present invention excludes compounds in which each of N and/or N' is a deoxyribonucleotide. In some embodiments the 5' terminal nucleotide of N or 2 or 3 consecutive of N and 1, 2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

Unless otherwise indicated, in preferred embodiments of the structures discussed herein the covalent bond between each consecutive N and N' is a phosphodiester bond.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar. Such structures are disclosed in PCT patent publication WO 2007/091269, assigned to the assignee of the present invention and incorporated herein in its entirety by reference.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain preferred embodiments a covalent bond is a phosphodiester bond. Covalent bond encompasses non-phosphorus-containing internucleoside linkages, such as those disclosed in WO 2004/041924 inter alia. Unless otherwise indicated, in preferred embodiments of the structures discussed herein the covalent bond between each consecutive N and N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to a target sequence. In other embodiments (N)x is substantially complementary to a target sequence.

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

In one aspect the present invention provides a compound having Structure (I):

(I) 5' (N)x-Z 3' (antisense strand)
3' Z'—(N')y-z" 5' (sense strand)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent, but if present is a capping moiety covalently attached at the 5' terminus of (N')y;

wherein x=18 to 27;
wherein y=18 to 27;

wherein (N)x comprises modified and unmodified ribonucleotides, each modified ribonucleotide having a 2'OMe on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide;

wherein in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond; and wherein the sequence of (N')y is a sequence substantially complementary to (N)x; and wherein the sequence of (N)x comprises an antisense sequence substantially complementary to 18 to 27 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533). In some embodiments x=y=19. In other embodiments x=y=21. In some embodiments the at least one unconventional moiety is present at positions 15, 16, 17, or 18 in (N')y. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments The compound comprises an L-DNA moiety at position 17, position 18 or positions 17 and 18.

In other embodiments the unconventional moiety is an abasic moiety. In various embodiments (N')y comprises at least five abasic ribose moieties or abasic deoxyribose moieties.

In yet other embodiments (N')y comprises at least five abasic ribose moieties or abasic deoxyribose moieties and at least one of N' is an LNA.

In some embodiments (N)x comprises nine alternating modified ribonucleotides. In other embodiments of Structure (I) (N)x comprises nine alternating modified ribonucleotides further comprising a 2'O modified nucleotide at position 2. In some embodiments (N)x comprises 2'OMe modified ribonucleotides at the odd numbered positions 1, 3, 5, 7, 9, 11, 13, 15, 17, 19. In other embodiments (N)x further comprises a 2'OMe modified ribonucleotide at one or both of positions 2 and 18. In yet other embodiments (N)x comprises 2'OMe modified ribonucleotides at positions 2, 4, 6, 8, 11, 13, 15, 17, 19.

hi various embodiments z" is present and is selected from an abasic ribose moiety, a deoxyribose moiety; an inverted abasic ribose moiety, a deoxyribose moiety; C6-amino-Pi; a mirror nucleotide.

In another aspect the present invention provides a compound having Structure (J) set forth below:

(J) 5' (N)x-Z 3' (antisense strand)
3' Z'—(N')y-z" 5' (sense strand)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent but if present is a capping moiety covalently attached at the 5' terminus of (N')y;

wherein x=18 to 27;
wherein y=18 to 27;

wherein (N)x comprises modified or unmodified ribonucleotides, and optionally at least one unconventional moiety;

wherein in (N')y at least one unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond; and wherein the sequence of (N')y is a sequence substantially complementary to (N)x; and wherein the sequence of (N)x comprises an antisense sequence substantially complementary to 18 to 27 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533).

In some embodiments x=y=19. In other embodiments x=y=21. In some preferred embodiments (N)x comprises modified and unmodified ribonucleotides, and at least one unconventional moiety.

In some embodiments in (N)x the N at the 3' terminus is a modified ribonucleotide and (N)x comprises at least 8 modified ribonucleotides. In other embodiments at least 5 of the at least 8 modified ribonucleotides are alternating beginning at the 3' end. In some embodiments (N)x comprises an abasic moiety in one of positions 5, 6, 7, 8, 9, 10, 11, 12, 13, 14 or 15.

In some embodiments the at least one unconventional moiety in (N')y is present at positions 15, 16, 17, or 18. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18. In other embodiments the at least one unconventional moiety in (N')y is an abasic ribose moiety or an abasic deoxyribose moiety.

In yet another aspect the present invention provides a compound having Structure (K) set forth below:

(K) 5' (N)x—Z 3' (antisense strand)
3' Z'—(N')y-z" 5' (sense strand)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent but if present is a capping moiety covalently attached at the 5' terminus of (N')y;

wherein x=18 to 27; wherein y=18 to 27;

wherein (N)x comprises a combination of modified or unmodified ribonucleotides and unconventional moieties, any modified ribonucleotide having a 2'OMe on its sugar;

wherein (N')y comprises modified or unmodified ribonucleotides and optionally an unconventional moiety, any modified ribonucleotide having a 2'OMe on its sugar;

wherein the sequence of (N')y is a sequence substantially complementary to (N)x; and wherein the sequence of (N)x comprises an antisense sequence substantially complementary to 18 to 27 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533).

In some embodiments x=y=19. In other embodiments x=y=21. In some preferred embodiments the at least one preferred one unconventional moiety is present in (N)x and is an abasic ribose moiety or an abasic deoxyribose moiety. In other embodiments the at least one unconventional moiety is present in (N)x and is a non-base pairing nucleotide analog. In various embodiments (N')y comprises unmodified ribonucleotides. In some embodiments (N)x comprises at least five abasic ribose moieties or abasic deoxyribose moieties or a combination thereof. In certain embodiments (N)x and/or (N')y comprise modified ribonucleotides which do not base pair with corresponding modified or unmodified ribonucleotides in (N')y and/or (N)x.

In various embodiments the present invention provides an siRNA set forth in Structure (L):

(L) 5' (N)x—Z 3' (antisense strand)
3' Z'—(N')y 5' (sense strand)

wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein Z and Z' are absent;
wherein x=y=19;

wherein in (N')y the nucleotide in at least one of positions 15, 16, 17, 18 and 19 comprises a nucleotide selected from an abasic unconventional moiety, a mirror nucleotide, a deoxyribonucleotide and a nucleotide joined to an adjacent nucleotide by a 2'-5' internucleotide bond;

wherein (N)x comprises alternating modified ribonucleotides and unmodified ribonucleotides each modified ribonucleotide being modified so as to have a 2'OMe on its sugar and the ribonucleotide located at the middle position of (N)x being modified or unmodified, preferably unmodified; and wherein the sequence of (N')y is a sequence substantially complementary to (N)x; and wherein the sequence of (N)x comprises an antisense sequence substantially complementary to 18 to 27 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533).

In some embodiments of Structure (L), in (N')y the nucleotide in one or both of positions 17 and 18 comprises a modified nucleotide selected from an abasic unconventional moiety, a mirror nucleotide and a nucleotide joined to an adjacent nucleotide by a 2'-5' internucleotide bond. In some embodiments the mirror nucleotide is selected from L-DNA and L-RNA. In various embodiments the mirror nucleotide is L-DNA.

In various embodiments (N')y comprises a modified nucleotide at position 15 wherein the modified nucleotide is selected from a mirror nucleotide and a deoxyribonucleotide.

In certain embodiments (N')y further comprises a modified nucleotide or pseudo nucleotide at position 2 wherein the pseudo nucleotide may be an abasic unconventional moiety and the modified nucleotide is optionally a mirror nucleotide.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)x further comprises 2'O-Me modified ribonucleotides at one or both positions 2 and 18. In other embodiments (N)x comprises 2'OMe modified ribonucleotides at positions 2, 4, 6, 8, 11, 13, 15, 17, 19.

Other embodiments of Structures (L) are envisaged wherein x=y=21; in these embodiments the modifications for (N')y discussed above instead of being in positions 17 and 18 are in positions 19 and 20 for 21-mer oligonucleotide; similarly the modifications in positions 15, 16, 17, 18 or 19 are in positions 17, 18, 19, 20 or 21 for the 21-mer oligonucleotide. The 2'OMe modifications on the antisense strand are similarly adjusted. In some embodiments (N)x comprises 2'OMe modified ribonucleotides at the odd numbered positions (5' to 3'; positions 1, 3, 5, 7, 9, 12, 14, 16, 18, 20 for the 21 mer oligonucleotide [nucleotide at position 11 unmodified]. In other embodiments (N)x comprises 2'OMe modified ribonucleotides at positions 2, 4, 6, 8, 10, 12, 14, 16, 18, 20 [nucleotide at position 11 unmodified for the 21 mer oligonucleotide.

In some embodiments (N')y further comprises a 5' terminal cap nucleotide. In various embodiments the terminal cap moiety is selected from an abasic unconventional moiety, an inverted abasic unconventional moiety, an L-DNA nucleotide, and a C6-imine phosphate (C6 amino linker with phosphate at terminus).

In other embodiments the present invention provides a double stranded compound having Structure (N) set forth below:

(N) 5' $(N)_x$—Z 3' (antisense strand)
3' Z'—$(N')_y$ 5' (sense strand)
wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein Z and Z' are absent;

wherein each of x and y is independently an integer between 18 and 40;

wherein (N)x, (N')y or (N)x and (N')y comprise non base-pairing modified nucleotides such that (N)x and (N')y form less than 15 base pairs in the double stranded compound; and wherein the sequence of (N')y is a sequence substantially complementary to (N)x; and wherein the sequence of (N)x comprises an antisense sequence substantially complementary to 18 to 40 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533).

In other embodiments the present invention provides a compound having Structure (O) set forth below:

(O) 5' $(N)_x$—Z 3' (antisense strand)
3' Z'—$(N')_y$ 5' (sense strand)
wherein each of N is a nucleotide selected from an unmodified ribonucleotide, a modified ribonucleotide, an unmodified deoxyribonucleotide and a modified deoxyribonucleotide;

wherein each of N' is a nucleotide analog selected from a six membered sugar nucleotide, seven membered sugar nucleotide, morpholino moiety, peptide nucleic acid and combinations thereof;

wherein each of $(N)_x$ and $(N')_y$ is an oligonucleotide in which each consecutive N or N' is joined to the next N or N' by a covalent bond;

wherein Z and Z' are absent;

wherein each of x and y is independently an integer between 18 and 40;

wherein the sequence of (N')y is a sequence substantially complementary to (N)x; and wherein the sequence of (N)x comprises an antisense sequence substantially complementary to 18 to 27 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533). In other embodiments the present invention provides a compound having Structure (P) set forth below:

(P) 5' $(N)_x$—Z 3' (antisense strand)
3' Z'—$(N')_y$ 5' (sense strand)
wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein Z and Z' are absent;

wherein each of x and y is independently an integer between 18 and 40;

wherein one of N or N' in an internal position of (N)x or (N')y or one or more of N or N' at a terminal position of (N)x or (N')y comprises an abasic moiety or a 2' modified nucleotide;

wherein the sequence of (N')y is a sequence substantially complementary to (N)x; and wherein the sequence of (N)x comprises an antisense sequence substantially complementary to 18 to 27 consecutive ribonucleotides in an mRNA set forth in any one of SEQ ID NOS:1-3. Preferably (N)x comprises an antisense sequence substantially identical to an antisense sequence set forth in any one of Tables A-H (SEQ ID NOS: 4-8,533). In various embodiments (N')y comprises a modified nucleotide at position 15 wherein the modified nucleotide is selected from a mirror nucleotide and a deoxyribonucleotide.

In certain embodiments (N')y further comprises a modified nucleotide at position 2 wherein the modified nucleotide is selected from a mirror nucleotide and an abasic unconventional moiety.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments $(N)_x$ further comprises 2'O-Me modified ribonucleotides at one or both positions 2 and 18. In other embodiments (N)x comprises 2'OMe modified ribonucleotides at positions 2, 4, 6, 8, 11, 13, 15, 17, 19.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar.

Said triple-stranded oligonucleotide may be an oligoribonucleotide having the general structure:

| 5' | Oligo1 (sense) | LINKER A | Oligo2 (sense) | 3' |
|---|---|---|---|---|
| 3' | Oligo1 (antisense) | LINKER B | Oligo3 (sense) | 5' |
| 3' | Oligo3 (antisense) | LINKER C | Oligo2 (antisense) | 5' |
| or | | | | |
| 5' | Oligo1 (sense) | LINKER A | Oligo2 (antisense) | 3' |
| 3' | Oligo1 (antisense) | LINKER B | Oligo3 (sense) | 5' |
| 3' | Oligo3 (antisense) | LINKER C | Oligo2 (sense) | 5' |
| or | | | | |
| 5' | Oligo1 (sense) | LINKER A | Oligo3 (antisense) | 3' |
| 3' | Oligo1 (antisense) | LINKER B | Oligo2 (sense) | 5' |
| 5' | Oligo3 (sense) | LINKER C | Oligo2 (antisense) | 3' | wherein one or more of linker A, linker B or linker C is present; any combination of two or more oligonucleotides and one or more of linkers A-C is possible, so long as the polarity of the strands and the general structure of the molecule remains. Further, if two or more of linkers A-C are present, they may be identical or different.

Thus, a triple-armed structure is formed, wherein each arm comprises a sense strand and complementary antisense strand (i.e. Oligo1 antisense base pairs to Oligo1 sense etc.). The triple armed structure may be triple stranded, whereby each arm possesses base pairing.

Further, the above triple stranded structure may have a gap instead of a linker in one or more of the strands. Such a molecule with one gap is technically quadruple stranded and not triple stranded; inserting additional gaps or nicks will lead to the molecule having additional strands. Preliminary results obtained by the inventors of the present invention indicate that said gapped molecules are more active in inhibiting certain target genes than the similar but non-gapped molecules. This may also be the case for nicked molecules.

According to one preferred embodiment of the invention, the antisense and the sense strands of the siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

Any siRNA sequence disclosed herein can be prepared having any of the modifications/structures disclosed herein. The combination of sequence plus structure is novel and can be used in the treatment of the conditions disclosed herein.

Lists of preferred siRNA are provided in Tables A-H infra. The separate lists of 19-mer, 21-mer and 23-mer siRNAs are prioritized based on their score according to a proprietary algorithm as the best sequences for targeting the human gene expression. Methods, molecules and compositions, which inhibit target genes are discussed herein at length, and any of said molecules and/or compositions are beneficially employed in the treatment of a patient suffering from any of said conditions. Tables A, C, F1, G and H set forth 19-mer oligomers. Tables B, D and F2, set forth 21-mer oligomers. Tables E1, E2, F3 and F4, set forth 23-mer oligomers.

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound which is capable of reducing the expression of a gene or the activity of the product of such gene to an extent sufficient to achieve a desired biological or physiological effect. The term "inhibitor" as used herein refers to one or more of an oligonucleotide inhibitor, including siRNA, shRNA, miRNA and ribozymes. Inhibition may also be referred to as down-regulation or, for RNAi, silencing.

The term "inhibit" as used herein refers to reducing or down-regulating the expression of a gene or the activity of the product of such gene to an extent sufficient to achieve a desired biological or physiological effect. Inhibition may be complete or partial.

"Nucleotide" is meant to encompass deoxyribonucleotides and ribonucleotides, which may be natural or synthetic, and be modified or unmodified. Modifications include changes and substitutions to the sugar moiety, the base moiety and/or the internucleotide linkages.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application mRNA sequences are set forth as representing the target of their corresponding genes. The terms "mRNA polynucleotide sequence" and mRNA are used interchangeably.

"Oligonucleotide" or "oligomer" refers to a deoxyribonucleotide or ribonucleotide sequence from about 2 to about 50 nucleotides. Each DNA or RNA nucleotide is independently natural or synthetic, and/or modified or unmodified. Modified nucleotide includes inter alia a mirror nucleotide (such as L-DNA or L-RNA). Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides and combinations thereof.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

The present invention provides methods and compositions for inhibiting expression of a target gene in vivo. In general, the method includes administering oligoribonucleotides, in particular small interfering RNAs (i.e., siRNAs) or a nucleic acid material that can produce siRNA in a cell to target an mRNA; in an amount sufficient to down-regulate expression of the Nrf2 target gene by an RNA interference mechanism. In particular, the method is useful for inhibiting expression of the Nrf2 gene for treatment of a subject suffering from a disease related to expression of that gene. In accordance with the present invention, the siRNA molecules or inhibitors of the target gene are used as drugs to treat various pathologies.

All analogs of, or modifications to, a nucleotide/oligonucleotide may be employed with the present invention, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a minor nucleotide including L-DNA and L-RNA. Figure 22 shows the chemical structure of a C6-amino phosphate 5' capping moiety and its attachment point to the 5' terminal (N').

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including LNA and ethylene bridged nucleic acids.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate.

Inverted abasic deoxyribose moiety includes inverted deoxyriboabasic; 3',5' inverted deoxyabasic 5'-phosphate.

Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU). The mirror nucleotide is a ribonucleotide (L-RNA) or a deoxyribonucleotide (L-DNA) and may further comprise at least one sugar or base modification and/or a backbone modification, such as a phosphorothioate or phosphonate moiety. U.S. Pat. No. 6,602,858 discloses nucleic acid catalysts comprising at least one L-nucleotide substitution.

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Bridged nucleic acids include LNA (2'-O,4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

In some embodiments of the present invention a preferred unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

The nucleotides are selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. Abasic pseudo-nucleotides are encompassed by the present invention. A nucleotide monomer comprising a modified base, including abasic pseudo-nucleotide monomers, may be substituted for one or more ribonucleotides of the oligonucleotide. An abasic pseudo-nucleotide monomer may be included at the one or more of the terminal positions or as a 5' terminal cap. A 5' terminal cap may also be selected from an inverted abasic pseudo-nucleotide analog, an L-DNA nucleotide, and a C6-imine phosphate.

In addition, analogues of polynucleotides are prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA comprises with a polyamide backbone which is similar to that found in peptides. PNA analogs have been shown to be resistant to enzymatic degradation and to have extended lives in vivo and in vitro.

Possible modifications to the sugar residue are manifold and include 2'-O alkyl, locked nucleic acid (LNA), glycol nucleic acid (GNA), threose nucleic acid (TNA), arabinoside; altritol (ANA) and other 6-membered sugars including morpholinos, and cyclohexinyls.

LNA compounds are disclosed in PCT Patent Publication Nos. WO 00/47599, WO 99/14226, and WO 98/39352. Examples of siRNA compounds comprising LNA nucleotides are disclosed in Elmen et al., (NAR 2005. 33(1):439-447) and in PCT Patent Publication No. WO 2004/083430. Six-membered ring nucleotide analogs are disclosed in Allart, et al (Nucleosides & Nucleotides, 1998, 17:1523-1526; and Perez-Perez, et al., 1996, Bioorg. and Medicinal Chem Letters 6:1457-1460) Oligonucleotides comprising 6-membered ring nucleotide analogs including hexitol and altritol nucleotide monomers are disclosed in PCT Patent Publication No. WO 2006/047842.

The compounds of the present invention are synthesized using one or more inverted nucleotides, for example inverted thymidine or inverted adenine (for example see Takei, et al., 2002. JBC 277(26):23800-06.

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetate derivatives. Certain structures include siRNA compounds having one or a plurality of 2'-5' internucleotide linkages (bridges or backbone).

In some embodiments, neither $(N)_x$ nor $(N')_y$ are phosphorylated at the 3' and 5' termini. In other embodiments either or both $(N)_x$ and $(N')_y$ are phosphorylated at the 3' termini (3' Pi). In yet another embodiment, either or both $(N)_x$ and $(N')_y$ are phosphorylated at the 3' termini with non-cleavable phosphate groups. In yet another embodiment, either or both $(N)_x$ and $(N')_y$ are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

An "aptamer" is an RNA or DNA single-strand or double-strand oligonucleic acid which binds to a target protein and does not generally exhibit non-specific effects. Aptamers can be modified for stability or other desired qualities in accordance with the nucleic acid modifications disclosed herein and/or known to one of skill in the art. Modifications to an aptamer are introduced anywhere in the molecule, such as the 5' or 3' termini, or at any internally defined modification site. For example, RNA aptamers can be stabilized with 2'-fluoro or 2'-amino modified pyrimidines. Aptamers can also be linked to reporter molecules or linker chemistries and can be attached to beads or other solid support if necessary (e.g. 5' or 3' amino, thiol ester or biotin groups). Thioaptamers are aptamers which contain sulfur modifications at specific internucleoside phosphoryl sites, and may possess enhanced stability, nuclease resistance, target affinity and/or selectivity. Examples of thioaptamers include phosphoromonothioate (S-ODN) and phosphorodithioate (S2-ODN) oligodeoxy thioaptamers. For further information on aptamers and thioaptamers see for example U.S. Pat. Nos. 5,218,088 and 6,423,493.

Oligonucleotides

Tables A-H (SEQ ID NOS: 4-8,533) comprise nucleic acid sequences of sense and corresponding antisense oligomers, useful in preparing siRNA compounds. The compounds are used as chemically and or structurally modified compounds.

The selection and synthesis of siRNA corresponding to known genes has been widely reported: see for example Ui-Tei et al., J Biomed Biotechnol. 2006; 65052; Chalk et al., BBRC. 2004, 319(1):264-74; Sioud & Leirdal, Met. Mol Biol. 2004, 252:457-69; Levenkova et al., Bioinform. 2004, 20(3):430-2; Ui-Tei et al., NAR. 2004, 32(3):936-48. For examples of the use and production of modified siRNA see for example Braasch et al., Biochem. 2003, 42(26):7967-75; Chiu et al., RNA. 2003, 9(9):1034-48; PCT Patent Publication Nos. WO 2004/015107 and WO 02/44321 and U.S. Pat. Nos. 5,898,031 and 6,107,094.

The present invention provides double-stranded oligonucleotides (e.g. siRNAs), which down-regulate the expression of a desired gene. A siRNA of the invention is a duplex oligoribonucleotide in which the sense strand is derived from the mRNA sequence of the desired gene, and the antisense strand is at least substantially complementary to the sense strand. In general, some deviation from the target mRNA sequence is tolerated without compromising the siRNA activity (see e.g. Czauderna et al., NAR. 2003, 31(11):2705-2716). A siRNA of the invention inhibits gene expression on a post-transcriptional level with or without destroying the mRNA. Without being bound by theory, siRNA may target the mRNA for specific cleavage and degradation and/or may inhibit translation from the targeted message.

In some embodiments an oligonucleotide pair selected from Tables A-H comprises modified siRNA, having one or more of any of the modifications disclosed herein. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid which is mRNA transcribed from a target gene, and the second strand comprises a ribonucleotide sequence at least partially complementary to the first strand and wherein said first strand and or said second strand comprises a plurality of groups of modified ribonucleotides, optionally having a modification at the 2'-position of the sugar moiety whereby within each strand each group of modified ribonucleotides is flanked on one or both sides by a group of flanking nucleotides, optionally ribonucleotides, whereby each ribonucleotide forming the group of flanking ribonucleotides is selected from an unmodified ribonucleotide or a ribonucleotide having a modification different from the modification of the groups of modified ribonucleotides.

In some embodiments the group of modified ribonucleotides and/or the group of flanking nucleotides comprises a number of ribonucleotides selected from the group consisting of an integer from 1 to 12. Accordingly, the group thus comprises one nucleotide, two nucleotides, three nucleotides, four nucleotides, five nucleotides, six nucleotides, seven nucleotides, eight nucleotides, nine nucleotides, ten nucleotides, eleven nucleotides or twelve nucleotides.

The groups of modified nucleotides and flanking nucleotides may be organized in a pattern on one or both of the strands. In some embodiments the antisense and sense strands comprise alternating unmodified and 2' sugar modified ribonucleotides. In some preferred embodiments the middle ribonucleotide in the antisense strand is an unmodified nucleotide. For example, in a 19-oligomer antisense strand, ribonucleotide at position 10 is unmodified; in a 21-oligomer antisense strand, the ribonucleotide at position 11 is unmodified; and in a 23-oligomer antisense strand, ribonucleotide at position 12 is unmodified. The modifications or pattern of modification, if any, of the siRNA must be planned to allow for this. In an even-numbered oligomer, e.g. a 22 mer, the middle nucleotide may be at position 11 or 12.

Possible modifications on the 2' moiety of the sugar residue include amino, fluoro, methoxy alkoxy, alkyl, amino, fluoro, chloro, bromo, CN, CF, imidazole, caboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1. One or more deoxyribonucleotides are also tolerated in the compounds of the present invention. As used herein, in the description of any strategy for the design of molecules, RNAi or any embodiment of RNAi disclosed herein, the term "end modification" or "terminal cap" refers to a chemical entity added to the terminal 5' or 3' nucleotide of the sense and/or antisense strand. Examples for such end modifications include, but are not limited to, 3' or 5' phosphate, inverted abasic, abasic, amino, fluoro, chloro, bromo, CN, $CF_3$, methoxy, imidazolyl, caboxylate, phosphothioate, $C_1$ to $C_{22}$ and lower alkyl, lipids, sugars and polyaminoacids (i.e. peptides), substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$; $N_3$; heterocycloalkyl; heterocycloalkaryl; aminoalkylamino; polyalkylamino or substituted silyl, as, among others, described in European patents EP 0 586 520 B1 or EP 0 618 925 B1.

In some embodiments the siRNA is blunt ended, i.e. Z and Z' are absent, on one or both ends. More specifically, the siRNA may be blunt ended on the end defined by the 5'-terminus of the first strand and the 3'-terminus of the second strand, and/or the end defined by the 3'-terminus of the first strand and the 5'-terminus of the second strand.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 5 nucleotides.

The length of RNA duplex is from about 18 to about 40 ribonucleotides, preferably 19, 21 or 23 ribonucleotides. Further, the length of each strand may independently have a length selected from the group consisting of about 15 to about 40 bases, preferably 18 to 23 bases and more preferably 19, 21 or 23 ribonucleotides.

In certain embodiments the complementarity between said first strand and the target nucleic acid is perfect. In some embodiments, the strands are substantially complementary, i.e. having one, two or up to five mismatches between said first strand and the target mRNA or between the first and the second strands. Substantially complementary refers to complementarity of greater than about 70%, and less than 100% to another sequence. For example in a duplex region consisting of 19 base pairs one mismatch results in 94.7% complementarity, two mismatches results in about 89.5% complementarity, 3 mismatches results in about 84.2% complementarity, 4 mismatches results in about 79% complementarity and 5 mismatches results in about 74% complementarity, rendering the duplex region substantially complementary. Accordingly, substantially identical refers to identity of greater than about 70%, to another sequence.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 2-100 nucleobases, preferably about 2 to about 30 nucleobases.

In preferred embodiments of the compounds of the invention having alternating ribonucleotides modified in at least one of the antisense and the sense strands of the compound, for 19 mer and 23 mer oligomers the ribonucleotides at the 5' and 3' termini of the antisense strand are modified in their sugar residues, and the ribonucleotides at the 5' and 3' termini of the sense strand are unmodified in their sugar residues. For 21 mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, it is preferred that the middle nucleotide of the antisense strand is unmodified.

According to one preferred embodiment of the invention, the antisense and the sense strands of the oligonucleotide/siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

The siRNA compounds disclosed herein are prepared having any of the modifications/structures disclosed herein. The combination of sequence plus structure is novel and is useful used in the treatment of the conditions disclosed herein.

Pharmaceutical Compositions

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different siRNAs.

In certain embodiments the siRNA of the present invention is chemically modified and is delivered as naked siRNA. The term "naked siRNA" refers to siRNA molecules that are free from any delivery vehicle that acts to assist, promote or facilitate entry into the cell, including viral sequences, viral particles, liposome formulations, lipofectin, nanoparticles or precipitating agents and the like. For example, siRNA in water or PBS is "naked siRNA". Accordingly, the present invention provides a pharmaceutical composition comprising chemically modified, naked siRNA; and a pharmaceutically acceptable carrier.

The invention further provides a pharmaceutical composition comprising at least one compound of the invention covalently or non-covalently bound to one or more compounds of the invention in an amount effective to inhibit the target genes of the present invention; and a pharmaceutically acceptable carrier. In some embodiments the compound is processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to inhibit expression in a cell of a human target gene of the present invention, the compound comprising a sequence which is substantially complementary to 18-40 consecutive nucleotides of the target gene mRNA.

Additionally, the invention provides a method of inhibiting the expression of the target gene of the present invention by at least 20%, preferably 30%, even more preferably 40% or even 50%, 60%, 70%, 80%, 90%, 95%, 98% or 100% as compared to a control comprising contacting an mRNA transcript of the target gene of the present invention with one or more of the compounds of the invention.

In one embodiment the oligoribonucleotide is inhibiting the target gene of the present invention, whereby the inhibition is selected from the group comprising inhibition of gene function, inhibition of polypeptide and inhibition of mRNA expression.

In one embodiment the compound inhibits the target polypeptide, whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridization or microarray hybridization, inter alia).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual subject, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, surfactants as well as similar pharmaceutical vehicles. In a particular embodiment, the administration comprises intravenous administration. In another embodiment the administration comprises topical or local administration. In addition, in certain embodiments the compositions for use in the novel treatments of the present invention may be formed as an aerosol, for example for intranasal administration.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules comprise a double-stranded nucleic acid structure as described herein, wherein the two siRNA sequences are selected from Tables A to H.

In another embodiment, the siRNA molecules are comprised of a double-stranded nucleic acid structure, wherein the first siRNA sequence is selected from Tables A to H, and the second siRNA molecule targets another cancer-related gene, thereby providing beneficial activity. The tandem double-stranded structure, which comprises two or more siRNA sequences, is processed intracellularly to form two or more different siRNAs. Such second siRNA molecule is for example an siRNA molecule that targets a cancer-related gene. Preferred cancer-related genes are for example gene encoding growth factors such as insulin-like growth factor (IGF), epidermal growth factor (EGF), fibroblast growth factor (FGF) and platelet derived growth factor (PDGF).

The siRNA molecules are covalently or non-covalently bound or joined by a linker to form a tandem siRNA molecule. Such tandem siRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem molecule comprised of two or more sequences which encompass siRNA produced via internal cellular processing, e.g., long dsRNAs, is also envisaged, as is a tandem molecule encoding two or more siRNA or shRNA molecules. Such tandem molecules are also considered to be a part of the present invention.

In some embodiments siRNA molecules that target Nrf2 are the main active component in a pharmaceutical composition, or are one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. In some embodiments, simultaneous inhibition of Nrf2 and said additional gene(s) provide an additive or synergistic effect for treatment of the diseases disclosed herein.

In a preferred embodiment, the one or more additional siRNA molecules target a cancer-related gene, thus providing an additive or synergistic effect with the Nrf2 siRNA. In another embodiment, the additional siRNA molecules target one or more of the cancer-related genes defined above.

In some embodiments the pharmaceutical composition comprises a sIRNA compound according to the present invention and a chemotherapeutic agent.

As disclosed herein, an aptamer is useful in the present invention in combination with one or more of the novel siRNA compounds disclosed herein for targeting Nrf2 and for the treatment of any one of the conditions disclosed herein. For example, an aptamer can be used with any one of the siRNA compounds disclosed herein in combination therapy for the treatment of the conditions disclosed herein. In some embodiments the pharmaceutical composition employed for such a combination therapy, which is also part of the present invention, comprises a siRNA of the present invention covalently or non-covalently attached to an aptamer.

Methods of Treatment

In another aspect, the present invention relates to a method for the treatment of a subject in need of treatment for a disease or disorder associated with the abnormal expression of Nrf2, comprising administering to the subject an amount of an inhibitor which reduces or inhibits expression of Nrf2.

In preferred embodiments the subject being treated is a warm-blooded animal and, in particular, mammals including human.

The methods of the invention comprise administering to the subject one or more inhibitory compounds which down-regulate the expression of Nrf2; and in particular siRNA in a therapeutically effective dose so as to thereby treat the subject.

In various embodiments the inhibitor is siRNA. The term "treatment" refers to both therapeutic treatment and prophylactic or preventative measures, wherein the object is to prevent or slow down (lessen) related disorders as listed herein. Those in need of treatment include those already experiencing the disease or condition, those prone to having the disease or condition, and those in which the disease or condition is to be prevented. The compounds of the invention may be administered before, during or subsequent to the onset of the disease or condition or symptoms associated therewith. In cases where treatment is for the purpose of prevention, then the present invention relates to a method for delaying the onset of or averting the development of the disease or disorder.

The present invention relates to the use of compounds which down-regulate the expression of Nrf2 particularly to novel small interfering RNAs (siRNAs), in the treatment of the following diseases or conditions in which inhibition of the expression of Nrf2 is beneficial.

The invention further provides a vector capable of expressing any of the aforementioned oligoribonucleotides in unmodified form in a cell.

The invention also provides a composition comprising one or more of the compounds of the invention in a carrier, preferably a pharmaceutically acceptable carrier. This composition may comprise a mixture of two or more different siRNAs.

The invention also provides a composition which comprises the above compound of the invention covalently or non-covalently bound to one or more compounds of the invention in an amount effective to inhibit Nrf2 and a carrier. In some embodiments the composition is processed intracellularly by endogenous cellular complexes to produce one or more oligoribonucleotides of the invention.

More particularly, the invention provides an oligoribonucleotide wherein one strand comprises consecutive nucleotides having, from 5' to 3', the sequence set forth in Tables A, C, F1, G and H (19 mer siRNA molecules) or in Tables B, D and F2 (21 mer siRNA molecules), or in Tables E1, E2, F3 and F4 (23 mer siRNA molecules), or a homolog thereof wherein in up to 2 of the nucleotides in each terminal region a base is altered. Preferred 19 mer siRNA molecules comprising the sense and corresponding antisense sequences are listed in Tables H1-H5 (SEQ ID NOS: 8,490-8,533).

The terminal region of the oligonucleotide refers to bases 1-4 and/or 16-19 in the 19-mer sequence and to bases 1-4 and/or 18-21 in the 21-mer sequence.

The siRNA molecules of the present invention may be delivered to the target tissue (such as the lung) by direct application of the naked molecules admixed with a carrier or a diluent using an aerosol. For administration via the upper respiratory tract, the composition is formulated into a solution, e.g., water or isotonic saline, buffered or unbuffered, or as a suspension, at an appropriate concentration for oro-nasal i.e. by intubation, intratracheal, intranasal, administration as an aerosol. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's Pharmaceutical Sciences 16th edition, Ed. Arthur Osol, page 1445 (1980)). One skilled in the art can readily determine a suitable saline content and pH for an innocuous aqueous solution for nasal, intratracheal and/or tipper respiratory administration.

Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compositions may contain minor amounts of polymers, surfactants, or other excipients well known to those of the art. In this context, "minor amounts" means no auxiliary agents or substances are present that might affect or mediate uptake of nucleic acid in the cells of the lungs.

Aerosol dosage, formulations and delivery systems are selected for a particular therapeutic application, as described, for example, in Gonda, "Aerosols for delivery of therapeutic and diagnostic agents to the respiratory tract," in Critical Reviews in Therapeutic Drug Carrier Systems, 6:273-313, 1990; and in Moren, "Aerosol dosage forms and formulations," in: Aerosols in Medicine, Principles, Diagnosis and Therapy, Moren, et al., Eds. Elsevier, Amsterdam, 1985. The term "aerosol" as used herein refers to any preparation of a fine mist of particles, which can be in solution or a suspension, whether or not it is produced using a propellant. Aerosols can be produced using standard techniques, such as ultrasonication or high pressure treatment.

Various suitable devices and methods of inhalation which can be used to administer particles to a patient's respiratory tract are known in the art. Nebulizers create a fine mist from a solution or suspension, which is inhaled by the patient. The devices described in U.S. Pat. No. 5,709,202 to Lloyd, et al., can be used. An MDI typically includes a pressurized canister having a meter valve, wherein the canister is filled with the solution or suspension and a propellant. The solvent itself may function as the propellant, or the composition may be combined with a propellant, such as freon. The composition is a fine mist when released from the canister due to the release in pressure. The propellant and solvent may wholly or partially evaporate due to the decrease in pressure. Other types of nebulizers which can be used to administer the molecules of the invention to a patient's respiratory tract are disclosed in co-pending PCT application number PCT/IL2008/000522, incorporated herein by reference.

Delivery systems aimed specifically at the enhanced and improved delivery of siRNA into mammalian cells have been developed, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 I 132-138. Respiratory formulations for siRNA are described in U.S. patent application No. 2004/0063654 of Davis et al. Cholesterol-conjugated siRNAs (and other steroid and lipid conjugated siRNAs) can been used for delivery see Soutschek et al Nature 432: 173-177(2004); and Lorenz et al. Bioorg. Med. Chemistry. Lett. 14:4975-4977 (2004).

The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations are particularly preferred.

The term "treatment" as used herein refers to administration of a therapeutic substance effective to ameliorate symptoms associated with a disease, to lessen the severity or cure the disease, or to prevent the disease from occurring. Thus "treatment" refers to both therapeutic treatment and prophylactic or preventative measures, wherein the object is to prevent or slow down (lessen) a disease in particular a cancerous disease such as lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. In a particular embodiment, the cancer is lung cancer such as non-small-cell lung carcinoma (NSCLC) or small-cell lung carcinoma.

In another aspect, the present invention provides a pharmaceutical composition comprising any of the above oligoribonucleotides or vectors and a pharmaceutically acceptable carrier. Another aspect of the invention is the use of a therapeutically effective amount of any of the above oligoribonucleotides or vectors for the preparation of a medicament for treating a patient suffering from a cancerous disease.

"Cancer and "cancerous disease" are used interchangeably and refer to a disease that is caused by or results in inappropriately high levels of cell division, inappropriately low levels of apoptosis, or both. Examples of cancerous diseases include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, amgiosarcoma, endotheliosarcoma, lymphangio sarcoma, lymphangioendotheliosarcoma, synovioma, mesothelioma, Ewing's tumor, leiomyo sarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, crailiopharyngioma, ependymoma, pinealoma, hemangioblastoma, acoustic neuroma, oligodenroglioma, schwamioma, meningioma, melanoma, neuroblastoma, and retinoblastoma). In some preferred embodiments the compounds of the present invention are useful in treating lung cancer and metastases in the lung.

As used herein, the term "proliferative disease" refers to any disease in which cellular proliferation, either malignant or benign, contributes to the pathology of the condition. Such unwanted proliferation is the hallmark of cancer and many chronic inflammatory diseases, thus examples of "proliferative disease" include the cancers listed supra and chronic inflammatory proliferative diseases such as psoriasis, inflammatory bowel disease and rheumatoid arthritis; proliferative cardiovascular diseases such as restenosis; proliferative ocular disorders such as diabetic retinopathy; and benign hyperproliferative diseases such as hemangiomas.

In one embodiment, the present invention provides a pharmaceutical composition comprising an Nrf2 inhibitory molecule, preferable an siRNA molecule that decreases the expression of the Nrf2 gene in combination with a chemotherapeutic agent. Without being bound by theory, since Nrf2 positively regulates drug detoxification enzymes, targeting this molecule may have a broad effect on all anticancer drugs. In various embodiments, the Nrf2 inhibitory molecule is administered prior to, concurrently with, or following administration of a chemotherapeutic. Without wishing to be bound by theory, administration of an Nrf2 inhibitory molecule likely enhances the accumulation or efficacy of a chemotherapeutic agent.

Compositions and methods of the invention may be used in combination with any conventional therapy known in the art. In one embodiment, the Nrf2 inhibitory molecules of the invention may be used in combination with cancer therapy known in the art. Thus the Nrf2 inhibitors may be used before, during or following cancer therapy. Exemplary cancer therapies include, for example, chemotherapy, cryotherapy, hormone therapy, growth factor inhibitors, radiotherapy, and surgery. Chemotherapeutic agents include abiraterone acetate, altretamine, anhydrovinbiastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-l-L-proline-t-butylamide, cachectin, cernadotin, chiorambucil, cyclophosphamide, 3',4'-didehydro-4'-deoxy-8'-norvincaleukoblastine, docetaxol, doxetaxel, cyclophosphamide, carboplatin, carmustine (BCNTJ), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, oxaliplatin paclitaxel, prednimustine, procarbazine, RPR1 09881, satrapaltin, stramustine phosphate, tamoxifen, tasonermin, taxol, tretinoin, vinbiastine, vincristine, vindesine sulfate, and vinflunine. Other examples of chemotherapeutic agents can be found in Cancer Principles and Practice of Oncology by V. T. Devita and S. Heliman (editors), 6th edition (Feb. 15, 2001), Lippincott Williams & Wilkins Publishers. A preferred combination according to the present invention is an siRNA molecule targeting Nrf2 with platinum drugs, more preferably an siRNA molecule set forth in Table C with a platinum drug, preferably carboplatin. Without being bound by theory, the Nrf2 siRNA inhibitors of the invention are found to be efficient promoters for the antineoplastic potential of platinum drugs, causing additive/synergistic effects in cancer cells. Platinum drugs include carboplatin, cisplatin, oxaliplatin and satrapaltin inter alia; see Kelland and Farrell, Platinum-based drugs in cancer therapy (Cancer drug discovery & development) Lavoisier 2000, which is hereby incorporated by reference.

The compounds which reduce or prevent the cancerous or proliferative disease, such as lung cancer, e.g. the novel siRNAs inter alia are preferably administered directly to the inner lung as naked siRNA in a vehicle such as PBS or other physiological solutions, but may alternatively be administered with a delivery vehicle as described above.

The present invention also provides for a process of preparing a pharmaceutical composition, which comprises:
obtaining one or more double stranded compound of the invention; and
admixing said compound with a pharmaceutically acceptable carrier, thereby obtaining the pharmaceutical compositions of the invention The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention delivered as naked siRNA. In another embodiment the compound is conjugated to a steroid or to a lipid or to another suitable delivery molecule e.g. to cholesterol.

Oligonucleotide Synthesis

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48: 2223-2311, Beaucage and Iyer, Tetrahedron 1993; 49: 6123-6194 and Caruthers et. al., Methods Enzymol. 1987; 154: 287-313; the synthesis of thioates is, among others, described in Eckstein F., Annu. Rev. Biochem. 1985; 54: 367-402, the synthesis of RNA molecules is described in Sproat, in Humana Press 2005 edited by Herdewijn; Kap. 2: 17-31 and respective downstream processes are, among others, described in Pingoud A. et. al., in IRL Press 1989 edited by Oliver; Kap. 7: 183-208 and Sproat, in Humana Press 2005 edited by Herdewijn; Kap. 2: 17-31 (supra).

Other synthetic procedures are known in the art e.g. the procedures as described in Usman et al., 1987, J. Am. Chem. Soc., 109, 7845; Scaringe et al., 1990, Nucleic Acids Res., 18, 5433; Wincott et al., 1995, Nucleic Acids Res. 23, 2677-2684; and Wincott et al., 1997, Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as disclosed herein.

The oligonucleotides of the present invention can be synthesized separately and joined together post-synthetically, for example, by ligation (Moore et al., 1992, *Science* 256, 9923; Draper et al., PCT Patent Publication No. WO93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via a tandem synthesis methodology, as described in US Patent Application Publication No. US2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

Additionally, in some embodiments the siRNA disclosed herein or any nucleic acid molecule comprising or encoding the siRNA is linked or bound (covalently or non-covalently) to an antibody or aptamer against a cell surface internalizable molecule expressed on a target cell, in order to achieve enhanced targeting for treatment of the diseases disclosed herein. For example, an anti-Fas antibody (preferably a neutralizing antibody) is combined (covalently or non-covalently) with a Nrf2 siRNA molecule for administering to a subject in need thereof. In another example, an aptamer which can act like a ligand/antibody is combined (covalently or non-covalently) with a Nrf2 siRNA molecule.

The term "Covalent bonding" as used herein refers to chemical bonding that is characterized by the sharing of pairs of electrons between atoms.

The term "Noncovalent bonding" as used herein refers to a variety of interactions that are not covalent in nature between molecules or parts of molecules that provide force to hold the molecules or parts of molecules together, usually in a specific orientation or conformation. These noncovalent interactions include: ionic bonds, hydrophobic interactions, hydrogen bonds, Van der Waals forces and dipole-dipole bonds.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an Nrf2 gene. In particular, it is envisaged that this oligonucleotide comprises sense and antisense siRNA sequences present in Tables A-H (SEQ ID NOS: 4-8,533).

As used herein, the term "inhibition" of the Nrf2 gene means inhibition of the gene expression (transcription or translation) or polypeptide activity.

Screening of Inactivation Compounds for Nrf2:

Some of the compounds and compositions of the present invention may be used in a screening assay for identifying and isolating compounds that modulate the activity of the Nrf2 gene, in particular compounds that modulate a disorder accompanied by an elevated level of Nrf2. The compounds to be screened comprise inter alia substances such as small chemical molecules and antisense oligonucleotides.

The inhibitory activity of the compounds of the present invention on Nrf2 expression may be used to determine the interaction of an additional compound with the target polypeptide, e.g., if the additional compound competes with the oligonucleotides of the present invention for inhibition of Nrf2, or if the additional compound rescues said inhibition. The inhibition or activation can be tested by various means, such as, inter alia, assaying for the product of the activity of the Nrf2 polypeptide or displacement of binding compound from the Nrf2 polypeptide in radioactive or fluorescent competition assays.

The present invention is illustrated in detail below with reference to the Examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series. Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996, Blood 87:3822.) Methods of performing RT-PCR are also well known in the art.

Example 1

Generation of Sequences for Active siRNA Compounds

Using proprietary algorithms and the known sequence of Nrf2 (gi2014957), the sense and antisense sequences of many potential siRNAs were generated. These sequences are listed in Tables A-H (set forth in SEQ ID NOS: 4-8,533). Tables A, C, F1, G and H show a list of 19-mers siRNAs specific to Nrf2 which are either human-specific, or human and cross-species with other species. Tables B, D and F2 show a list of 21-mers siRNAs specific to Nrf2 winch are either human-specific, or human and cross-species with other species. Tables E1, E2, F3 and F4 show a list of 23-mers siRNAs specific to Nrf2 which are either human-specific, or human and cross-species with other species. All siRNAs are depicted in 5' to 3' orientation, and the sense and complementary antisense sequences are depicted on the same line in the tables.

Example 2

In Vitro Testing of siRNA Compounds for Nrf2

1. General 1.5-2×10$^5$ tested cells (HeLa or 293 cells) are seeded per well in a 6-well plate (70-80% confluent).

About 24 h later, cells were transfected with siRNA oligos using lipofectamine 2000 reagent (Invitrogene) at a final concentration of 500 pM, 5 nM, 20 nM or 40 nM. The cells were incubated at 37° C. in a $CO_2$ incubator for 72 h.

As positive control for cell transfection, PTEN-Cy3 labeled siRNA oligos were used. As negative control for siRNA activity, GFP siRNA oligos were used. About 72 h after transfection cells were harvested and RNA was extracted from cells. Transfection efficiency was tested by fluorescent microscopy.

The percent of inhibition of gene expression using specific preferred siRNAs was determined by using qPCR analysis of target gene in cells expressing the endogenous gene. Tables H1-H5 below listed the currently preferred sequences which were tested in vitro for inhibition of Nrf2 expression.

TABLE H1 sense and antisense oligonucleotides are in the 5'-3' orientation

| Active siRNA | Sequence |
| --- | --- |
| NFE2L2_10 (Sense: SEQ ID NO: 8490; Antisense SEQ ID NO: 8499) | Sense: CCCUGUCGAAAAAAUCAUU Antisense: AAUGAUUUUUCGACAGGG having one mismatch (underlined) compared to the human sequence |
| NFE2L2_4 (Sense: SEQ ID NO: 8491; Anitsense:SEQ ID NO: 8500) | Sense: CCAUUCACAAAAGACAAA Antisense: UUUGUCUUUUGUGAAUGGG |
| NFE2L2_5 (Sense: SEQ ID NO: 8492; Antisense: SEQ ID NO: 8501) | Sense: CAGCAGGACAUGGAUUUGA Antisense: UCAAAUCCAUGUCCUGCUG |
| NFE2L2_9 (Sense: SEQ ID NO: 8493; Antisense: SEQ ID NO: 8502) | Sense: UCCCUGUCGAAAAAAUCAU Antisense: AUGAUUUUUUCCACAGGGA |
| NFE2L2_11 (Sense: SEQ ID NO: 8494; Antisense: SEQ ID 8503) | Sense: CCUGUCGAAAAAAUCAUUA Antisense: UAAUGAUUUUUUCGACAGG |
| NFE2L2_1 (Sense: SEQ ID NO: 8495; Antisense: SEQ ID NO: 8504) | Sense: GGAGGGGUAAGAAUAAAGU Antisense: ACUUUAUUCUUACCCCUCC |
| NFE2L2_2 (Sense: SEQ ID NO: 8496; Antisense: SEQ ID NO: 8505) | Sense: GCCCUCACCUGCUACUUUA Antisense: UAAAGUAGCAGGUGAGGGC |
| NFE2L2_3 (Sense: SEQ ID NO: 8497; Antisense: SEQ ID NO: 8506) | Sense: UCCCGUUUCUACAUGACAA Antisense: UUGUCAUCUACAAACCGGA |
| NFE2L2_12 (Sense: SEQ ID NO: 8498; Antisense: SEQ ID NO: 8507) | Sense: GUAAGAAGCCAGAUGUUAA Antisense: UUAACAUCUGGCUUCUUAC |

TABLE H2 sense and antisense oligonucleotides are in the 5'-3' orientation. All molecules in Table H2 were modified with alternating 2-O-methyl modification in both strands.

| SiRNA number | Sense | Antisense | Residual activity in vitro |
| --- | --- | --- | --- |
| NFE2L2_4 | CCCAUUCACAAAAGACAAA SEQ ID NO: 8491 | UUUGUCUUUUGUGAAUGGG SEQ ID NO: 8500 | 20 |
| NFE2L2_5 | CAGCAGGACAUGGAUUUGA SEQ ID NO: 8492 | UCAAAUCCAUGUCCUGCUG SEQ ID NO: 8501 | 30 |
| NFE2L2_9 | UCCCUGUCGAAAAAAUCAU SEQ ID NO: 8493 | AUGAUUUUUUCGACAGGGA SEQ ID NO: 8502 | 56 |
| NFE2L2_10 | CCCUGUCGAAAAAAUCAUU SEQ ID NO: 8490 | AAUGAUUUUUCGACAGGG SEQ ID NO: 8499 | 9 |

TABLE H2-continued sense and antisense oligonucleotides are in the
5'-3' orientation. All molecules in Table H2 were
modified with alternating 2-O-methyl modification in both strands.

| SiRNA number | Sense | Antisense | Residual activity in vitro |
|---|---|---|---|
| NFE2L2_11 | CCUGUCGAAAAAAUCAUUA; SEQ ID NO: 8494 | UAAUGAUUUUUUCGACAGG SEQ ID NO: 8503 | 54 |
| NFE2L2_1 | GGAGGGGUAAGAAUAAAGU SEQ ID NO: 8495 | ACUUUAUUCUUACCCCUCC SEQ ID NO: 8504 | 27 |
| NFE2L2_2 | GCCCUCACCUGCUACUUUA SEQ ID NO: 8496 | UAAAGUAGCAGGUGAGGGC SEQ ID NO: 8505 | 8 |
| NFE2L2_3 | UCCCGUUUGUAGAUGACAA SEQ ID NO: 8497 | UUGUCAUCUACAAACGGGA SEQ ID NO: 8506 | 4 |
| NFE2L2_12 | GUAAGAAGCCAGAUGUUAA SEQ ID NO: 8498 | UUAACAUCUGGCUUCUUAC SEQ ID NO: 8507 | 4 |
| NFE2L2_13 | CCCUGUAGAAAAAAUCAUU SEQ ID NO: 8508 | AAUGAUUUUUUCUACAGGG SEQ ID NO: 8521 | 11 |
| NFE2L2_14 | CCUGGAAGUGUCAAACAGA SEQ ID NO: 8509 | UCUGUUUGACACUUCCAGG SEQ ID NO: 8522 | |
| NFE2L2_16 | GGGCAAAAGCUCUCCAUAU SEQ ID NO: 8510 | AUAUGGAGAGCUUUUGCCC SEQ ID NO: 8523 | |
| NFE2L2_18 | CUGGAAGUGUCAAACAGAA SEQ ID NO: 8511 | UUCUGUUUGACACUUCCAG SEQ ID NO: 8524 | |
| NFE2L2_19 | UGAGCUGGAAAAACAGAAA SEQ ID NO: 8512 | UUUCUGUUUUUCCAGCUCA SEQ ID NO: 8525 | |
| NFE2L2_20 | GAGCUGGAAAAACAGAAAA SEQ ID NO: 8513 | UUUUCUGUUUUUCCAGCUC SEQ ID NO: 8526 | |
| NFE2L2_21 | ACAAAAGACAAACAUUCAA SEQ ID NO: 8514 | UUGAAUGUUUGUCUUUUGU SEQ ID NO: 8527 | |
| NFE2L2_24 | CAUUCACAAAAGACAAACA SEQ ID NO: 8515 | UGUUUGUCUUUUGUGAAUG SEQ ID NO: 8528 | |
| NFE2L2_26 | GCAGGACAUGGAUUUGAUU SEQ ID NO: 8516 | AAUCAAAUCCAUGUCCUGC SEQ ID NO: 8529 | |
| NFE2L2_28 | AGCAGGACAUGGAUUUGAU SEQ ID ND: 8517 | AUCAAAUCCAUGUCCUGCU SEQ ID NO: 8530 | |
| NFE2L2_30 | GACAUGGAUUUGAUUGACA SEQ ID NO: 8518 | UGUCAAUCAAAUCCAUGUC SEQ ID NO: 8531 | |
| NFE2L2_32 | AGGGCAAAAGCUCUCCAUA SEQ ID NO: 8519 | UAUGGAGAGCUUUUGCCCU SEQ ID NO: 8532 | |
| NFE2L2_33 | AGGUUGCCCACAUUCCCAA SEQ ID NO: 8520 | UUGGGAAUGUGGGCAACCU SEQ ID NO: 8533 | |

TABLE H3

All modifications preformed on the NFE2L2_3 molecule ( Sen: SEQ ID NO: 8497; AS: SEQ ID NO: 8506). Sense strand is 5'-3'orientation; Antisense strand is 3'-5' orientation.
The molecules in Table H3 were modified as following:
Bold: 2-O-methyl sugar modified ribonucleotide
<u>underlined</u>: ENA (2'-O,4'-C-Ethylene-bridged nucleotide)
small case: L-DNA
\*: 2'-5' internucleosidelinkage; 3'p: phosphate in the 3' end; ^: PACE linkage.
Table H3.

| SiRNA number and ID | Description of modifications | | Residual activity in vitro at 20nM (% of control) |
|---|---|---|---|
| NFE2L2_3 | Sense: | 5'- <u>U</u>CCCGUUUGUAGAUGACAA | 30% |
|  | Antisense: | 3'- AGGGCAAACAUCUACUGUU |  |
| NFE2L2_3 | Sense: | 5'- <u>UC</u>CCGUUUGUAGAUGACAA | 36% |
|  | Antisense: | 3'- AGGGCAAACAUCUACUGUU |  |
| NFE2L2_3 | Sense: | 5'- <u>UCC</u>CGUUUGUAGAUGACAA | 45% |
|  | Antisense: | 3'- AGGGCAAACAUCUACUGUU |  |
| NFE2L2_3 | Sense: | 5'- <u>UCCC</u>GUUUGUAGAUGACaa | 6% |
|  | Antisense: | 3'- AGGGCAAACAUCUACUGUU |  |
| NFE2L2_3 | Sense: | 5'- <u>UCCC</u>GUUUGUAGAUGAcaA | 24% |
|  | Antisense: | 3'- AGGGCAAACAUCUACUGUU |  |
| NFE2L2_3 | Sense: | 5'- <u>UCCC</u>GUUUGUAGAUGAC\*A\*A | 11% |
|  | Antisense: | 3'- AGGGCAAACAUCUACUGUU |  |
| NFE2L2_3 | Sense: | 5'- <u>UCCC</u>GUUUGUAGAUGA\*C\*AA | 34% |
|  | Antisense: | 3'- AGGGCAAACAUCUACUGUU |  |
| NFE2L2_3 | Sense: | 5'- <u>UCCC</u>GUUUGUAGAUGACAA | 41% |
|  | Antisense | 3'- <u>AGGG</u>CAAACAUCUACUGUU |  |
| NFE2L2_3 | Sense: | 5'- <u>UCCC</u>GUUUGUAGAUGACAA | 35% |
|  | Antisense: | 3'- <u>AGGG</u>CAAACAUCUACUGUU |  |
| NFE2L2_3 | Sense: | 5'- <u>UCCC</u>GUUUGUAGAUGACAA | 50% |
|  | Antisense: | 3'- <u>AGGG</u>CAAACAUCUACUGUU |  |
| NFE2L2_3 | Sense: | 5'- <u>UCCC</u>GUUUGUAGAUGACaa | 32% |
|  | Antisense: | 3'- <u>AGGG</u>CAAACAUCUACUGUU |  |
| NFE2L2_3 | Sense: | 5'- <u>UCCC</u>GUUUGUAGAUGAcaA | 49% |
|  | Antisense: | 3'- <u>AGGG</u>CAAACAUCUACUGUU |  |
| NFE2L2_3 | Sense: | 5'- <u>UCCC</u>GUUUGUAGAUGAC\*A\*A | 38% |
|  | Antisense: | 3'- <u>AGGG</u>CAAACAUCUACUGUU |  |
| NFE2L2_3 | Sense: | 5'- <u>UCCC</u>GUUUGUAGAUGA\*C\*AA | 58% |
|  | Antisense: | 3'- <u>AGGG</u>CAAACAUCUACUGUU |  |
| NFE2L2_3 | Sense: | 5'- UCCCGUUUGUAGAUGAC\*A\*A | 12% |
|  | Antisense: | 3'- AGGGCAAACAUCUACUGUU |  |
| NFE2L2_3 | Sense: | 5'- UCCCGUUUGUAGAUGAC\*A\*A-3'p | 15% |
|  | Antisense: | 3'- AGGGCAAACAUCUACUGUU |  |
| NFE2L2_3 | Sense: | 5'- UCCCGUUUGUAGAUGACaa-3'p | 13% |
|  | Antisense: | 3'- AGGGCAAACAUCUACUGUU |  |
| NFE2L2_3 | Sense: | 5'- UCCCGUUUGUAGAUGACaa | 9% (in 5nM) |
|  | Antisense: | 3'- AGGGCAAACAUCUACUGUU |  |
| NFE2L2_3 | Sense: | 5'- UCCCGUUUGUAGAUGACaa-3'p | 13% |
|  | Antisense: | 3'- AGGGCAAACAUCUACUGUU |  |
| NFE2L2_3 | Sense: | 5'- UCCCGUUUGUAGAUGACaa | 21% |
|  | Antisense: | 3'- AGGGCAAACAUCUACUGUU |  |
| NFE2L2_3 | Sense: | 5'- UCCCGUUUGUAGAUGAC^A^A | 5% |
|  | Antisense: | 3'- AGGGCAAACAUCUACUGUU |  |
| NFE2L2_3 | Sense: | 5'- U C CCGUUUGUAGAUGACAA | 22% |
|  | Antisense: | 3'- AGGGCAAACAUCUACUGUU |  |

TABLE H3-continued

All modifications preformed on the NFE2L2_3 molecule ( Sen: SEQ ID
NO: 8497; AS: SEQ ID NO: 8506). Sense strand is 5'-3'orientation;
Antisense strand is 3'-5' orientation.
The molecules in Table H3 were modified as following:
Bold: 2-O-methyl sugar modified ribonucleotide
<u>underlined</u>: ENA (2'-O,4'-C-Ethylene-bridged nucleotide)
small case: L-DNA
\*: 2'-5' internucleosidelinkage; 3'p: phosphate in the 3' end; ^: PACE linkage.
Table H3.

| SiRNA number and ID | Description of modifications | | Residual activity in vitro at 20nM (% of control) |
|---|---|---|---|
| NFE2L2_3 | Sense: | 5'- U C CCGUUUGUAGAUGAC^A^A | 8% |
| | Antisense: | 3'- AGGGCAAACAUCUACUGUU | |
| NFE2L2_3 | Sense: | 5'- U^C^CCGUUUGUAGAUGAC^AA | 7% |
| | Antisense: | 3'- AGGGCAAACAUCUACUGUU | |
| NFE2L2_3 | Sense: | 5'- U^C^CCGUUUGUAGAUGACA^A | 9% |
| | Antisense: | 3'- AGGGCAAACAUCUACUGUU | |
| NFE2L2_3 | Sense: | 5'- U^C^CCGUUUGUAGAUGAC^AA | 7% |
| | Antisense: | 3'- AGGGCAAACAUCUACUGUU | |
| NFE2L2_3 | Sense: | 5'- UCCCGUUUGUAGAUGAC^A^A | 15% |
| | Antisense: | 3'- A^G^GGCAAACAUCUACUGUU | |
| NFE2L2_3 | Sense: | 5'- U^C^CCGUUUGUAGAUGACAA | 16% |
| | Antisense: | 3'- A^G^GGCAAACAUCUACUGUU | |
| NFE2L2_3 | Sense: | 5'- U^C^CCGUUUGUAGAUGAC^A^A | 49% |
| | Antisense: | 3'- A^G^GGCAAACAUCUACUGUU | |
| NFE2L2_3 | Sense: | 5'- U^C^CCGUUUGUAGAUGA^C^AA | 25% |
| | Antisense: | 3'- A^G^GGCAAACAUCUACUGUU | |
| NFE2L2_3 | Sense: | 5'- UCCCGUUUGUAGAUGACA^A | 49% |
| | Antisense: | 3'- A^G^GGCAAACAUCUACUGUU | |
| NFE2L2_3 | Sense: | 5'- UCCCGUUUGUAGAUGAC^AA | 49% |
| | Antisense: | 3'- A^G^GGCAAACAUCUACUGUU | |

: 2-O-methyl alternating structure in the antisense strand

TABLE H4

All modifications preformed with the NFE2L2_14 (Sense: SEQ ID NO: 8509;
Antisense: SEQ ID NO: 8522) and NFE2L2_16 molecules (Sense: SEQ Id NO: 8510;
Antisense: SEQ ID NO: 8523).
Sense strand is 5'-3'orientation; Antisense strand is 3'-5' orientation.
The molecules in Table H4 were modified as following:
Bold: 2-O-methyl sugarmofdified ribonucleotide:
subscript: DNA nucleotide; small case: L-DNA
Table H4:

| SiRNA number and ID | Description of modifications | | Residual activity in vitro at 20nM (% of control) |
|---|---|---|---|
| NFE2L2_14 | Sense: | 5'- CCUGGAAGUGUCAAACagA | 8% |
| | Antisense: | 3'- GGACCUUCACAGUUUGUCU | |
| NFE2L2_14 | Sense: | 5'- CCUGGAAGUGUCAAACagA | 23% |
| | Antisense: | 3'- GGACCUUCACAGUUUGUCU | |
| NFE2L2_16 | Sense: | 5'- GGGCAAAAGCUCUCcAuaU | 20% |
| | Antisense: | 3'- CCCGUUUUCGAGAGGUAUA | |
| NFE2L2_16 | Sense: | 5'- GGGCAAAACCUCUCcAuaU | 41% |
| | Antisense: | 3'- CCCGUUUUCGAGAGGUAUA | |

: 2-O-methyl alternating structure in the antisense strand

The molecules in Table H5 NFE2L2_3 (Sense: SEQ ID NO: 8497; Antisense: SEQ ID NO: 8506). NFE2L2_14 (Sense: SEQ ID NO: 8509; Antisense: SEQ ID NO: 8522) and NFE2L2_16 (Sense: SEQ ID NO: 8510; Antisense: SEQ ID NO: 8523) were modified according to the key below:

| Modification Code | Modification Name |
|---|---|
| $ | No 3' Phosphate |
| m | 2'OMe-3'-Pi |
| Ld | L-DNA-3'-Pi |
| ena | ENA-3'-Pi |
| dNpac | PACE |

-continued

| Modification Code | Modification Name |
|---|---|
| d | DNA-3'-Pi |
| iB | inverted-deoxy-Abasic |
| c6Np | Amino-C6-Pi |
| r | ribonucleotide |

TABLE 5

| SiRNA Number | Sense (5' > 3') | AntiSense (5' > 3') | % Residual Activity at 20 nM |
|---|---|---|---|
| NFE2L2__ | rU; rC; rC; rC; rG; rU; rU; rU; rG; rU; rA; rG; rA; rU; rG; rA; rC; LdA; LdA$ | rU; rU; rG; rU; rC; rA; rU; rC; rU; rA; rC; rA; rA; rA; rC; rG; rG; rG; LdA$ | 8 |
| NFE2L2__3 | rU; rC; rC; rC; rG; rU; rU; rU; rG; rU; rA; rG; rA; rU; rG; rA; rC2p; rA2p; rA$ | mU; rU; mG; rU; mC; rA; mU; rC; mU; rA; mC; rA; mA; rA; mC; rG; mG; rG; mA$ | 12 |
| NFE2L2__3 | rU; rC; rC; rC; rG; rU; rU; rU; rG; rU; rA; rG; rA; rU; rG; rA; rC2p; rA2p; rA | mU; rU; mG; rU; mC; rA; mU; rC; mU; rA; mC; rA; mA; rA; mC; rG; mG; rG; mA$ | 15 |
| NFE2L2__3 | rU; rC; rC; rC; rG; rU; rU; rU; rG; rU; rA; rG; rA; rU; rG; rA; rC; LdA; LdA | mU; rU; mG; rU; mC; rA; mU; rC; mU; rA; mC; rA; mA; rA; mC; rG; mG; rG; mA$ | 13 |
| NFE2L2__3 | rU; rC; rC; rC; rG; rU; rU; rU; rG; rU; rA; rG; rA; rU; rG; rA; rC; LdA; LdA$ | mU; rU; mG; rU; mC; rA; mU; rC; mU; rA; mC; rA; mA; rA; mC; rG; mG; rG; mA$ | 9 |
| NFE2L2__3 | mU; mC; mC; mC; mG; rU; rU; rU; rG; rU; rA; rG; rA; rU; rG; rA; rC; LdA; LdA | mU; rU; mG; rU; mC; rA; mU; rC; mU; rA; mC; rA; mA; rA; mC; rG; mG; rG; mA$ | 13 |
| NFE2L2__3 | mU; mC; mC; mC; mG; rU; rU; rU; rG; rU; rA; rG; rA; rU; rG; rA; rC; LdA; LdA$ | mU; rU; mG; rU; mC; rA; mU; rC; mU; rA; mC; rA; mA; rA; mC; rG; mG; rG; mA$ | 21 |
| NFE2L2__3 | rU; rC; rC; rC; rG; rU; rU; rU; rG; rU; rA; rG; rA; rU; rG; rA; dCpac; dApac; rA$ | mU; rU; mG; rU; mC; rA; mU; rC; mU; rA; mC; rA; mA; rA; mC; rG; mG; rG; mA$ | 5 |
| NFE2L2__3 | dUpac; dCpac; rC; rC; rG; rU; rU; rU; rG; rU; rA; rG; rA; rU; rG; rA; rC; rA; rA$ | mU; rU; mG; rU; mC; rA; mU; rC; mU; rA; mC; rA; mA; rA; mC; rG; mG; rG; mA$ | 22 |
| NFE2L2__3 | dUpac; dCpac; rC; rC; rG; rU; rU; rU; rG; rU; rA; rG; rA; rU; rG; rA; dCpac; dApac; rA$ | mU; rU; mG; rU; mC; rA; mU; rC; mU; rA; mC; rA; mA; rA; mC; rG; mG; rG; mA$ | 8 |
| NFE2L2__3 | rU; rC; rC; rC; rG; rU; rU; rU; rG; rU; rA; rG; rA; rU; rG; dApac; dCpac; rA; rA$ | mU; rU; mG; rU; mC; rA; mU; rC; mU; rA; mC; rA; mA; rA; mC; rG; mG; rG; mA$ | 7 |
| NFE2L2__3 | rU; rC; rC; rC; rG; rU; rU; rU; rG; rU; rA; rG; rA; rU; rG; rA; rC; dApac; rA$ | mU; rU; mG; rU; mC; rA; mU; rC; mU; rA; mC; rA; mA; rA; mC; rG; mG; rG; mA$ | 9 |
| NFE2L2__3 | rU; rC; rC; rC; rG; rU; rU; rU; rG; rU; rA; rG; rA; rU; rG; rA; dCpac; rA; rA$ | mU; rU; mG; rU; mC; rA; mU; rC; mU; rA; mC; rA; mA; rA; mC; rG; mG; rG; mA$ | 7 |
| NFE2L2__3 | rU; rC; rC; rC; rG; rU; rU; rU; rG; rU; rA; rG; rA; rU; rG; rA; dCpac; dApac; rA$ | rU; rU; rG; rU; rC; rA; rU; rC; rU; rA; rC; rA; rA; rA; rC; rG; dGpac; dGpac; rA$ | 15 |
| NFE2L2__3 | dUpac; dCpac; rC; rC; rG; rU; rU; rU; rG; rU; rA; rG; rA; rU; rG; rA; rC; rA; rA$ | rU; rU; rG; rU; rC; rA; rU; rC; rU; rA; rC; rA; rA; rA; rC; rG; dGpac; dGpac; rA$ | 16 |
| NFE2L2__3 | dUpac; dCpac; rC; rC; rG; rU; rU; rU; rG; rU; rA; rG; rA; rU; rG; rA; dCpac; dApac; rA$ | rU; rU; rG; rU; rC; rA; rU; rC; rU; rA; rC; rA; rA; rA; rC; rG; dGpac; dGpac; rA$ | 49 |
| NFE2L2__3 | rU; rC; rC; rC; rG; rU; rU; rU; rG; rU; rA; rG; rA; rU; rG; dApac; dCpac; rA; rA$ | rU; rU; rG; rU; rC; rA; rU; rC; rU; rA; rC; rA; rA; rA; rC; rG; dGpac; dGpac; rA$ | 25 |
| NFE2L2__3 | rU; rC; rC; rC; rG; rU; rU; rU; rG; rU; rA; rG; rA; rU; rG; rA; rC; dApac; rA$ | rU; rU; rG; rU; rC; rA; rU; rC; rU; rA; rC; rA; rA; rA; rC; rG; dGpac; dGpac; rA$ | 49 |
| NFE2L2__3 | rU; rC; rC; rC; rG; rU; rU; rU; rG; rU; rA; rG; rA; rU; rG; rA; dCpac; rA; rA$ | rU; rU; rG; rU; rC; rA; rU; rC; rU; rA; rC; rA; rA; rA; rC; rG; dGpac; dGpac; rA$ | 49 |
| NFE2L2__3 | enaT; rC; rC; rC; rG; rU; rU; rU; rG; rU; rA; rG; rA; rU; rG; rA; rC; rA; rA$ | mU; rU; mG; rU; mC; rA; mU; rC; mU; rA; mC; rA; mA; rA; mC; rG; mG; rG; mA$ | 30 |

TABLE 5-continued

| SiRNA Number | Sense (5' > 3') | AntiSense (5' > 3') | % Residual Activity at 20 nM |
|---|---|---|---|
| NFE2L2_3 | enaT; enaC; rC; rC; rG; rU; rU; rU; rG; rU; rA; rG; rA; rU; rG; rA; rC; rA; rA$ | mU; rU; mG; rU; mC; rA; mU; rC; mU; rA; mC; rA; mA; rA; mC; rG; mG; rG; mA$ | 36 |
| NFE2L2_3 | enaT; enaC; enaC; rC; rG; rU; rU; rU; rG; rU; rA; rG; rA; rU; rG; rA; rC; rA; rA$ | mU; rU; mG; rU; mC; rA; mU; rC; mU; rA; mC; rA; mA; rA; mC; rG; mG; rG; mA$ | 45 |
| NFE2L2_3 | enaT; enaC; enaC; rC; rG; rU; rU; rU; rG; rU; rA; rG; rA; rU; rG; rA; rC; LdA; LdA$ | mU; rU; mG; rU; mC; rA; mU; rC; mU; rA; mC; rA; mA; rA; mC; rG; mG; rG; mA$ | 6 |
| NFE2L2_3 | enaT; enaC; enaC; rC; rG; rU; rU; rU; rG; rU; rA; rG; rA; rU; rG; rA; LdC; LdA; rA$ | mU; rU; mG; rU; mC; rA; mU; rC; mU; rA; mC; rA; mA; rA; mC; rG; mG; rG; mA$ | 24 |
| NFE2L2_3 | enaT; enaC; enaC; rC; rG; rU; rU; rU; rG; rU; rA; rG; rA; rU; rG; rA; rC2p; rA2p; rA$ | mU; rU; mG; rU; mC; rA; mU; rC; mU; rA; mC; rA; mA; rA; mC; rG; mG; rG; mA$ | 11 |
| NFE2L2_3 | enaT; enaC; rC; rG; rU; rU; rU; rG; rU; rA; rG; rA; rU; rG; rA2p; rC2p; rA; rA$ | mU; rU; mG; rU; mC; rA; mU; rC; mU; rA; mC; rA; mA; rA; mC; rG; mG; rG; mA$ | 31 |
| NFE2L2_3 | enaT; rC; rC; rC; rG; rU; rU; rU; rG; rU; rA; rG; rA; rU; rG; rA; rC; rA; rA$ | rU; rU; rG; rU; rC; rA; rU; rC; rU; rA; rC; rA; rA; rA; rC; rG; enaG; enaG; enaA$ | 41 |
| NFE2L2_3 | enaT; enaC; rC; rC; rG; rU; rU; rU; rG; rU; rA; rG; rA; rU; rG; rA; rC; rA; rA$ | rU; rU; rG; rU; rC; rA; rU; rC; rU; rA; rC; rA; rA; rA; rC; rG; enaG; enaG; enaA$ | 35 |
| NFE2L2_3 | enaT; enaC; enaC; rC; rG; rU; rU; rU; rG; rU; rA; rG; rA; rU; rG; rA; rC; rA; rA$ | rU; rU; rG; rU; rC; rA; rU; rC; rU; rA; rC; rA; rA; rA; rC; rG; enaG; enaG; enaA$ | 50 |
| NFE2L2_3 | enaT; enaC; enaC; rC; rG; rU; rU; rU; rG; rU; rA; rG; rA; rU; rG; rA; rC; LdA; LdA$ | rU; rU; rG; rU; rC; rA; rU; rC; rU; rA; rC; rA; rA; rA; rC; rG; enaG; enaG; enaA$ | 32 |
| NFE2L2_3 | enaT; enaC; enaC; rC; rG; rU; rU; rU; rG; rU; rA; rG; rA; rU; rG; rA; LdC; LdA; rA$ | rU; rU; rG; rU; rC; rA; rU; rC; rU; rA; rC; rA; rA; rA; rC; rG; enaG; enaG; enaA$ | 49 |
| NFE2L2_3 | enaT; enaC; enaC; rC; rG; rU; rU; rU; rG; rU; rA; rG; rA; rU; rG; rA; rC2p; rA2p; rA$ | rU; rU; rG; rU; rC; rA; rU; rC; rU; rA; rC; rA; rA; rA; rC; rG; enaG; enaG; enaA$ | 38 |
| NFE2L2_3 | enaT; enaC; rC; rG; rU; rU; rU; rG; rU; rA; rG; rA; rU; rG; rA2p; rC2p; rA; rA$ | rU; rU; rG; rU; rC; rA; rU; rC; rU; rA; rC; rA; rA; rA; rC; rG; enaG; enaG; enaA$ | 58 |
| NFE2L2_14 | rC; rC; rU; rG; rG; rA; rA; rG; rU; rG; rU; rC; rA; rA; dA; rC; rA; LdG; rA$ | mU; rC; mU; rG; mU; rU; mU; rG; mA; rC; mA; rC; mU; rU; mC; rC; mA; rG; mG$ | 9; 17 (5 nM) |
| NFE2L2_14 | rC; rC; rU; rG; rG; rA; rA; rG; rU; rG; rU; rC; rA; rA; dA; rC; LdG; LdG; rA$ | mU; rC; mU; rG; mU; rU; mU; rG; mA; rC; mA; rC; mU; rU; mC; rC; mA; rG; mG$ | 23; 22 (5 nM) |
| NFE2L2_16 | rG; rG; rG; rC; rA; rA; rA; rA; rG; rC; rU; rC; rU; rC; dC; rA; rU; LdA; rU$ | mA; rU; mA; rU; mG; rG; mA; rG; mA; rG; mC; rU; mU; rU; mU; rG; mC; rC; mC$ | 20; 16 (5 nM) |
| NFE2L2_16 | rG; rG; rG; rC; rA; rA; rA; rA; rG; rC; rU; rC; rU; rC; dC; rA; Ld; LdA; rU$ | mA; rU; mA; rU; mG; rG; mA; rG; mA; rG; mC; rU; mU; rU; mU; rG; mC; rC; mC$ | 41; 47 (5 nM) |
| NFE2L2_14 | dC; mC; dT; mG; dG; mA; dA; mG; dT; mG; dT; mC; dA; mA; dA; mC; dA; mG; dA$ | mU; dC; mU; dG; mU; dT; mU; dG; mA; rC; mA; dC; mU; dT; mC; dC; mA; dG; mG$ | 84 |
| NFE2L2_14 | dC; mC; dT; mG; dG; mA; dA; mG; dT; mG; dT; dC; mA; dA; mA; dC; mA; dG; mA$ | dT; mC; dT; mG; dT; mU; dT; mG; rA; rC; mA; dC; mU; dT; mC; dC; mA; dG; mG$ | 43 |
| NFE2L2_14 | rC; LdC; rU; rG; rG; rA; rA; rG; rU; rG; rU; rC; rA; rA; rA; rC; rA; LdG; rA$ | mU; rC; mU; rG; mU; rU; mU; rG; mA; rC; mA; rC; mU; rU; mC; rC; mA; rG; mG$ | |
| NFE2L2_14 | iB; rC; rC; rU; rG; rG; rA; rA; rG; rU; rG; rU; rC; rA; rA; rA; rC; rA; LdG; rA$ | mU; rC; mU; rG; mU; rU; mU; rG; mA; rC; mA; rC; mU; rU; mC; rC; mA; rG; mG$ | |
| NFE2L2_14 | rC; LdC; rU; rG; rG; rA; rA; rG; rU; rG; rU; rC; rA; rA; rA; rC; rA; LdG; rA$; | rU; mC; rU; mG; rU; mU; rU; mG; rA; rC; mA; rC; mU; rU; mC; rC; mA; rG; mG$ | |
| NFE2L2_14 | rC; LdC; rU; rG; rG; rA; rA; rG; rU; rG; rU; rC; rA; rA; rA; rC; rA; LdG; rA$ | mU; mC; mU; rG; mU; rU; mU; rG; mA; mA; rC; mU; rU; mC; rC; mA; rG; mG$ | |
| NFE2L2_14 | rC; rC; rU; rG; rG; rA; rA; rG; rU; rG; rU; rC; rA; rA; rA; rC; rA; LdG; rA$ | mU; mC; mU; rG; mU; rU; mU; rG; mA; rC; mA; rC; mU; rU; mC; rC; mA; rG; mG$ | |
| NFE2L2_14 | rC; rC; rU; rG; rG; rA; rA; rG; rU; rG; rU; rC; rA; rA; rA; rC; rA; LdG; rA$ | mU; mC; mU; rG; mU; rU; mU; rG; mA; rC; mA; rC; mU; rU; mC; rC; mA; rG; mG$ | |

TABLE 5-continued

| SiRNA Number | Sense (5' > 3') | AntiSense (5' > 3') | % Residual Activity at 20 nM |
|---|---|---|---|
| NFE2L2__14 | rC; rC; rU; rG; rG; rA; rA; rG; rU; rG; rU; rC; rA; rA; rA; rC; rA; LdG; rA$; | rU; mC; rU; mG; rU; mU; rU; mG; rA; rC; mA; rC; mU; rU; mC; rC; mA; rG; mG$ | |
| NFE2L2__14 | iB; rC; rC; rU; rG; rG; rA; rA; rG; rU; rG; rU; rC; rA; rA; rA; rC; rA; LdG; rA$ | rU; mC; rU; mG; rU; mU; rU; mG; rA; rC; mA; rC; mU; rU; mC; rC; mA; rG; mG$ | |
| NFE2L2__14 | iB; rC; rC; rU; rG; rG; rA; rA; rG; rU; rG; rU; rC; rA; rA; rA; rC; rA; LdG; rA$ | mU; mC; mU; rG; mU; mU; rG; mA; rC; mA; rC; mU; rU; mC; rC; mA; rG; mG$ | |
| NFE2L2__14 | c6Np; rC; rC; rU; rG; rG; rA; rA; rG; rU; rG; rU; rC; rA; rA; rA; rC; rA; LdG; rA$ | mU; rC; mU; rG; mU; rU; mU; rG; mA; rC; mA; rC; mU; rU; mC; rC; mA; rG; mG$ | |
| NFE2L2__14 | c6Np; rC; rC; rU; rG; rG; rA; rA; rG; rU; rG; rU; rC; rA; rA; rA; rC; rA; LdG; rA$ | mU; mC; mU; rG; mU; rU; mU; rG; mA; rC; mA; rC; mU; rU; mC; rC; mA; rG; mG$ | |
| NFE2L2__14 | c6Np; rC; rC; rU; rG; rG; rA; rA; rG; rU; rG; rU; rC; rA; rA; rA; rC; rA; LdG; rA$ | rU; mC; rU; mG; rU; mU; rU; mG; rA; rC; mA; rC; mU; rU; mC; rC; mA; rG; mG$ | |

Example 3

The Effect of Nrf2 siRNA Treatment on Tumor Growth in Vivo Methods (a) Subcutaneous tumor xenografts: A549 cells ($5\times10^6$) are injected into the hind leg of male athymic nude mice and the subcutaneous tumor is measured weekly. The tumor volumes are measured using the following formula: [length (mm)× width (mm)×width (mm)×0.52]. For in vivo delivery of siRNA into subcutaneous tumors, siRNA duplexes diluted in PBS are injected into the hind leg tumors using insulin syringes at a concentration of 10 μg/ml. Intraperitoneal injections of carboplatin are given at a dose of 40 mg/kg body weight. Both siRNA and carboplatin are administered twice weekly for 4 weeks. In order to test the anti-tumor activity of Nrf2 siRNA in vivo, mice bearing subcutaneous tumors are treated with Nrf2 siRNA by direct injection into the tumor and by carboplatin twice a week for 4 weeks and tumor weight is measured at the termination of the experiment.

(b) Lung metastasis experiments: $2\times10^6$ A549-C8-luc cells are injected into SCID-Beige mice (Charles River, Mass.) intravenously and the lung tumor is measured weekly. For aerosol delivery of Nrf2 or GFP siRNA into lung tumors, 100 μg of siRNA duplex diluted in PBS is aerosolized using a nebulizer. Mice are given three dose of siRNA (100 μg/dose) every week, for 4 weeks, using a nebulizer. Intraperitoneal injections of carboplatin are given at a dose of 30 mg/kg body weight twice/week. Tumor weight is measured at the termination of the experiment.

siRNA according to Tables A-H, and in particular to siRNA disclosed in Tables H1-H5 are tested in this animal model, which show that these siRNA compounds may treat and/or prevent lung cancer.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08278287B2). An electronic copy of the "Sequence Listing" will also be available from the USPTO upon request and payment of the fee set forth in 37 CFR 1.19(b)(3).

What is claimed:

1. A double-stranded compound having the structure:
5' $(N)_x$—Z 3' (antisense strand)
3' Z'—$(N')_y$—Z" 5' (sense strand)
wherein each of N and N' is a nucleotide which may be an unmodified or a modified ribonucleotide, or may be an unconventional nucleotide moiety;
wherein each of $(N)_x$ and $(N')_y$ is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein Z" may be present or absent, but if present is a capping moiety covalently attached at the 5' terminus of $(N')_y$;
wherein x=y=19;
wherein $(N)_x$ comprises at least five alternating unmodified and modified ribonucleotides beginning at the 3' end of $(N)_x$ and at least nine modified ribonucleotides and unconventional nucleotide moieties in total and each remaining N is an unmodified ribonucleotide;
wherein $(N')_y$ comprises an unconventional nucleotide moiety which is selected from the group consisting of an L-DNA mirror nucleotide and a nucleotide joined to an adjacent nucleotide by a 2'-5' internucleotide phosphate bond in at least one of the 3' terminal position or the 3' penultimate position; and wherein the sequence of $(N)_x$ is 5' UUGUCAUCUACAAACGGGA 3' (SEQ ID NO: 8,506) and the sequence of $(N)_y$ is 5' UCCCGUUUGUAGAUGACAA 3' (SEQ ID NO: 8,497).

2. The double-stranded compound according to claim 1, wherein $(N')_y$ comprises an L-DNA mirror nucleotide at the 3' terminal position.

3. The double-stranded compound according to claim 1, wherein $(N')_y$ comprises an L-DNA mirror nucleotide at the 3' penultimate position.

4. The double-stranded compound according to claim 1, wherein the modified ribonucleotides in (N)x comprise 2'-O-methyl sugar modified ribonucleotides.

5. The double-stranded compound according to claim 1, wherein the unmodified ribonucleotides are present at positions 2, 4, 6, 8, 10, 12, 14, 16 and 18 and the 2'-O-methyl sugar modified ribonucleotides are present at positions 1, 3, 5, 7, 9, 11, 13, 15, 17 and 19.

6. The double-stranded compound according to claim 4 wherein the unmodified ribonucleotides are present at positions 1, 3, 5, 7, 9, 10, 12, 14, 16 and 18 and the 2'-O-methyl sugar modified ribonucleotide are present at positions 2, 4, 6, 8, 11, 13, 15, 17 and 19.

7. The double-stranded compound according to claim 1 wherein $(N')_y$ further comprises a bicyclic nucleotide.

8. The double-stranded compound according to claim 7 wherein the bicyclic nucleotide is a locked nucleic acid (LNA) or 2'-O, 4'-C-ethylene-bridged nucleic acid (ENA).

9. A composition comprising a pharmaceutically acceptable carrier and a double-stranded compound according to claim 1 in an amount effective to down-regulate expression of a human nuclear factor erythroid-2 related factor 2 (Nrf2) gene.

10. A method of treating a patient suffering from a disorder comprising administering to the patient the composition according to claim 9 in a therapeutically effective dose so as to thereby treat the patient.

11. The method of claim 10, wherein the disorder is cancer or a proliferative disease.

12. The method of claim 11, wherein the cancer is lung cancer.

13. The method according to claim 12, wherein the composition is administered as naked siRNA.

14. The method of claim 13, wherein the naked siRNA is administered via aerosol to the lung of the patient.

15. The method of claim 13, wherein the siRNA is administered via intubation or inhalation to the lung of the patient.

16. The method according to claim 10, further comprising administering to the patient a chemotherapy drug.

17. The method of claim 16, wherein the chemotherapy drug is a compound comprising platinum.

18. The double-stranded compound according to claim 2, wherein (N')y comprises a nucleotide joined to an adjacent nucleotide by a 2'-5' internucleotide phosphate bond at the 3' terminal position.

19. The double-stranded compound according to claim 2, wherein (N')y comprises a nucleotide joined to an adjacent nucleotide by a 2'-5' internucleotide phosphate bond at the 3' penultimate position.

20. The double-stranded compound according to claim 19, wherein (N')y comprises a nucleotide joined to an adjacent nucleotide by a 2'-5' internucleotide phosphate bond in positions 17 and 18.

21. The double-stranded compound of claim 1, wherein one or more of the nucleotides which form the 2'-5' phosphodiester bonds further comprises a 3'-O-methyl sugar modification.

* * * * *